(12) United States Patent
Pan et al.

(10) Patent No.: US 10,115,903 B2
(45) Date of Patent: Oct. 30, 2018

(54) EMITTER HAVING A CONDENSED RING SYSTEM

(71) Applicant: Merck Patent GmbH, Darmstadt (DE)

(72) Inventors: Junyou Pan, Frankfurt am Main (DE); Martin Engel, Darmstadt (DE); Herwig Buchholz, Frankfurt am Main (DE)

(73) Assignee: Merck Patent GmbH (DE)

( * ) Notice: Subject to any disclaimer, the term of this patent is extended or adjusted under 35 U.S.C. 154(b) by 441 days.

(21) Appl. No.: 14/652,982

(22) PCT Filed: Nov. 27, 2013

(86) PCT No.: PCT/EP2013/003585
§ 371 (c)(1),
(2) Date: Jun. 17, 2015

(87) PCT Pub. No.: WO2014/094965
PCT Pub. Date: Jun. 26, 2014

(65) Prior Publication Data
US 2016/0197275 A1    Jul. 7, 2016

(30) Foreign Application Priority Data

Dec. 18, 2012  (EP) .................................... 12008416

(51) Int. Cl.

| | | |
|---|---|---|
| H01L 51/00 | (2006.01) | |
| C09K 11/06 | (2006.01) | |
| C07D 249/20 | (2006.01) | |
| C07D 471/04 | (2006.01) | |
| C07D 495/04 | (2006.01) | |
| C07D 307/80 | (2006.01) | |
| C08F 12/22 | (2006.01) | |
| C08F 12/30 | (2006.01) | |
| C08F 12/32 | (2006.01) | |
| C09D 125/08 | (2006.01) | |
| C09D 125/18 | (2006.01) | |
| C09D 139/00 | (2006.01) | |
| A61N 5/06 | (2006.01) | |
| C08F 212/08 | (2006.01) | |
| C08F 224/00 | (2006.01) | |
| C08F 226/06 | (2006.01) | |
| C08F 228/06 | (2006.01) | |
| H01L 51/50 | (2006.01) | |
| H01L 51/52 | (2006.01) | |

(52) U.S. Cl.
CPC .......... *H01L 51/004* (2013.01); *A61N 5/0616* (2013.01); *C07D 249/20* (2013.01); *C07D 307/80* (2013.01); *C07D 471/04* (2013.01); *C07D 495/04* (2013.01); *C08F 12/22* (2013.01); *C08F 12/30* (2013.01); *C08F 12/32* (2013.01); *C08F 212/08* (2013.01); *C08F 224/00* (2013.01); *C08F 226/06* (2013.01); *C08F 228/06* (2013.01); *C09D 125/08* (2013.01); *C09D 125/18* (2013.01); *C09D 139/00* (2013.01); *C09K 11/06* (2013.01); *H01L 51/0043* (2013.01); *H01L 51/0052* (2013.01); *H01L 51/0072* (2013.01); *H01L 51/0073* (2013.01); *H01L 51/0074* (2013.01); *A61N 2005/0653* (2013.01); *C09K 2211/145* (2013.01); *C09K 2211/1425* (2013.01); *C09K 2211/1458* (2013.01); *C09K 2211/1466* (2013.01); *H01L 51/5004* (2013.01); *H01L 51/5012* (2013.01); *H01L 51/5206* (2013.01); *H01L 51/5221* (2013.01); *H01L 2251/552* (2013.01)

(58) Field of Classification Search
None
See application file for complete search history.

(56) References Cited

U.S. PATENT DOCUMENTS

| | | | | |
|---|---|---|---|---|
| 3,554,741 | A * | 1/1971 | Gipstein | ................. C08F 24/00 430/77 |
| 6,060,508 | A * | 5/2000 | Philippo | .............. C07D 307/79 514/443 |
| 7,217,774 | B2 * | 5/2007 | Litz | ........................ C08F 214/18 526/257 |
| 7,714,099 | B2 * | 5/2010 | Morishita | ............ C07D 209/88 313/504 |
| 7,723,553 | B2 * | 5/2010 | Pillow | .................. C07C 13/465 428/917 |
| 8,034,420 | B2 * | 10/2011 | Akino | .................. C08G 61/123 252/301.29 |
| 9,024,304 | B2 * | 5/2015 | Jeon | .................... H01L 51/0052 257/40 |
| 9,159,932 | B2 * | 10/2015 | Fujita | .................. H01L 51/0059 |
| 9,793,504 | B2 * | 10/2017 | Newsome | .......... H01L 51/0541 |
| 2004/0220182 | A1 * | 11/2004 | Mujica-Fernaud | ...... C07D 405/06 514/227.5 |
| 2005/0129980 | A1 | 6/2005 | Suzuki et al. | |
| 2005/0222352 | A1 | 10/2005 | Litz et al. | |
| 2009/0160327 | A1 * | 6/2009 | Oda | ....................... C09K 11/06 313/504 |
| 2009/0256139 | A1 * | 10/2009 | Wu | ..................... H01L 51/0036 257/40 |

(Continued)

FOREIGN PATENT DOCUMENTS

| | | |
|---|---|---|
| CN | 1723257 A | 1/2006 |
| CN | 102432756 A | 5/2012 |

(Continued)

OTHER PUBLICATIONS

Kuhn et al. (Org. let., v13(n15), 4100-4103, 2011) (Year: 2011).*

(Continued)

*Primary Examiner* — Kevin M Bernatz
(74) *Attorney, Agent, or Firm* — Drinker Biddle & Reath LLP

(57) ABSTRACT

The present invention relates to organic electroluminescent devices which comprise aromatic ring systems with two or three condensed rings as emitter materials, and to their possible uses.

10 Claims, 2 Drawing Sheets

(56) References Cited

U.S. PATENT DOCUMENTS

| | | | | |
|---|---|---|---|---|
| 2009/0314997 A1* | 12/2009 | Heeney | ............... | C07D 495/04 252/500 |
| 2010/0135073 A1* | 6/2010 | Lindner | ............... | B82Y 10/00 365/174 |
| 2011/0049478 A1* | 3/2011 | Meng | ............... | C07D 209/86 257/40 |
| 2011/0135903 A1 | 6/2011 | Suzuki et al. | | |
| 2011/0256422 A1* | 10/2011 | Reichelt | ............... | B82Y 10/00 428/704 |
| 2012/0056170 A1* | 3/2012 | Pan | ............... | H01L 51/004 257/40 |
| 2012/0068314 A1* | 3/2012 | Kastler | ............... | H01G 4/18 257/632 |
| 2012/0267579 A1* | 10/2012 | Hwang | ............... | B82Y 10/00 252/501.1 |
| 2013/0317475 A1 | 11/2013 | Eberle et al. | | |
| 2014/0061545 A1* | 3/2014 | Leroy | ............... | C09K 11/06 252/500 |
| 2015/0340612 A1* | 11/2015 | Pan | ............... | C09K 11/06 607/88 |

FOREIGN PATENT DOCUMENTS

| | | | |
|---|---|---|---|
| DE | 1906831 | A1 | 11/1969 |
| EP | 2075305 | A2 | 7/2009 |
| JP | H11130817 | A | 5/1999 |
| JP | 2005054079 | A | 3/2005 |
| JP | 2005149766 | A | 6/2005 |
| JP | 2005320512 | A | 11/2005 |
| JP | 2010054817 | A | 3/2010 |
| WO | WO-03044877 | A2 | 5/2003 |
| WO | WO-2004016708 | A1 | 2/2004 |
| WO | WO-2004055921 | A2 | 7/2004 |
| WO | WO-2009099290 | A2 | 8/2009 |
| WO | WO-2012107163 | A1 | 8/2012 |

OTHER PUBLICATIONS

Geary e tal. (Org. Let., v11(n23), 5478, 2009) (Year: 2009).*
International Search Report for PCT/EP2013/003585 dated Aug. 25, 2014.

* cited by examiner

EMITTER HAVING A CONDENSED RING SYSTEM

CROSS-REFERENCE TO RELATED APPLICATIONS

This application is a national stage application (under 35 U.S.C. § 371) of PCT/EP2013/003585, filed Nov. 27, 2013, which claims benefit of European Application No. 12008416.5, filed Dec. 18, 2012, both of which are incorporated herein by reference in their entirety.

The present invention relates to organic electroluminescent devices which comprise aromatic ring systems having two or three condensed rings as emitter materials, and to possible uses thereof.

The structure of organic light-emitting diodes (OLEDs) in which organic semiconductors are employed as functional materials is described, for example, in U.S. Pat. No. 4,539,507, U.S. Pat. No. 5,151,629, EP 0 676 461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). OLEDs represent a very highly promising technology for display screen and lighting applications. To this end, OLEDs are necessary which emit light in the visible region of the spectrum, i.e. typically red, green and blue light.

Furthermore, there are many applications which require light or radiation having even shorter wavelengths. Thus, for example, in the area of life science and medicine, wavelengths of in the range from 280 to 400 nm are necessary for so-called "cell imaging" or for biosensors. Furthermore, in the electronics industry, wavelengths from 300 to 400 nm are required for so-called "solid-state lighting" and from 300 to 365 nm, for example, for the curing of polymers and printing ink. Also of major importance are phototherapeutic applications in the medical or cosmetics sector. Many undesired skin changes and skin diseases can be treated by means of phototherapy. Wavelengths in the region of ultraviolet (UV) radiation are often required for this purpose. An example thereof is the treatment of the skin of psoriatic patients, for which purpose a radiation source which emits UV radiation of a wavelength of 311 nm is typically employed.

Mercury, deuterium, excimer and xenon lamps are typical, conventional UV radiation sources. However, they are unwieldy and some contain toxic substances which may cause soiling and may represent health risks. The conventional lamps therefore have disadvantages regarding safety, usability, handling ability and portability, which in turn results in limited possible applications. In addition, UV-LEDs are also commercially available. However, most of these LEDs are either at the research stage, only emit radiation having a wavelength greater than 365 nm or are very expensive. In addition, LEDs have the disadvantage that they are point emitters, which require relatively thick and rigid devices. Another class of radiation sources or light sources are the organic electroluminescent devices (for example OLEDs or OLECs—organic light-emitting electrochemical cells). In contrast to the other light and radiation sources, these are area emitters. Furthermore, the organic electroluminescent devices allow the production of flexible equipment, such as displays, lighting devices and irradiation devices. These devices are also particularly suitable for many applications owing to their efficiency and the simple and space-saving structure.

However, only very little is known to date about organic electroluminescent devices which emit radiation in the UV region. The emission of most organic electroluminescent devices is usually limited to wavelengths greater than 350 nm. In addition, the performance data of these devices are inadequate.

Chao et al. report (Adv. Mater. 17[8], 992-996. 2005.) on UV-OLEDs based on fluorene polymers having an electroluminescence emission wavelength greater than 360 nm;

Wong et al. report (Org. Lett. 7[23], 5131-5134. 2005) on UV-OLEDs based on spirobifluorene polymers having an electroluminescence emission wavelength at 360 nm or greater;

Zhou et al. report (Macromolecules 2007, 40 (9), 3015-3020) on UV-OLEDs comprising emitting polymers based on fluorene and tetraphenylsilane derivatives having an electroluminescence emission wavelength at 350 nm;

Shinar et al. report (Applied Surface Science 2007, 254 (3), 749-756) on UV-OLEDs using Bu-PBD as emitter having an electroluminescence emission wavelength of 350 nm.

Burrows reports (Applied Physics Letters 2006, 88 (18), 183503) on an OLED comprising 4,4'-bis (diphenylphosphine oxide) biphenyl as emitter. The device emits at 337 nm.

Sharma et al., report (Applied Physics Letters 2006, 88 (14), 143511-143513) on a UV-OLED which emits at 357 nm. The emitter used is based on polysilane.

For the above-mentioned reasons, it would be desrable to develop organic electroluminescent devices which emit radiation in the UV region, in particular in the lower UV-A region (315 to 380 nm) and in the UV-B region (280 to 315 nm). A particular challenge here is the provision of suitable organic emitter materials and the provision of organic electroluminescent devices comprising these emitters.

The object of the present invention is therefore to overcome the said disadvantages of the prior art by the provision of organic electroluminescent devices having the best-possible physical properties which exhibit an emission in the UV region.

Surprisingly, it has been found that certain compounds, described in greater detail below, achieve these objects and result in organic electroluminescent devices having unexpectedly good properties. The present invention therefore relates to organic electroluminescent devices which comprise compounds of this type.

The present invention provides organic electroluminescent devices which comprise at least two electrodes and at least one emitting layer (emitter layer) between the electrodes. The emitting layer here comprises at least one bi- or tricyclic aromatic or heteroaromatic compound of the general formula (1) or (2):

formula (1)

formula (2)

where the compound of the general formula (1) or (2) may be in substituted or unsubstituted form, and where the following applies to the symbols used:

Ar¹, Ar² and Ar³ each, independently of one another, denote an aromatic or heteroaromatic 5- or 6-membered ring, which is intended to be denoted by the circles surrounding the symbols, where at least one of the rings Ar¹, Ar² and Ar³ in the formula (2) is a five-membered ring and where the rings Ar¹ and Ar² in formula (1) and the rings Ar¹ and Ar³ or Ar² and Ar³ in formula (2) each have two common ring atoms.

Figure 1:
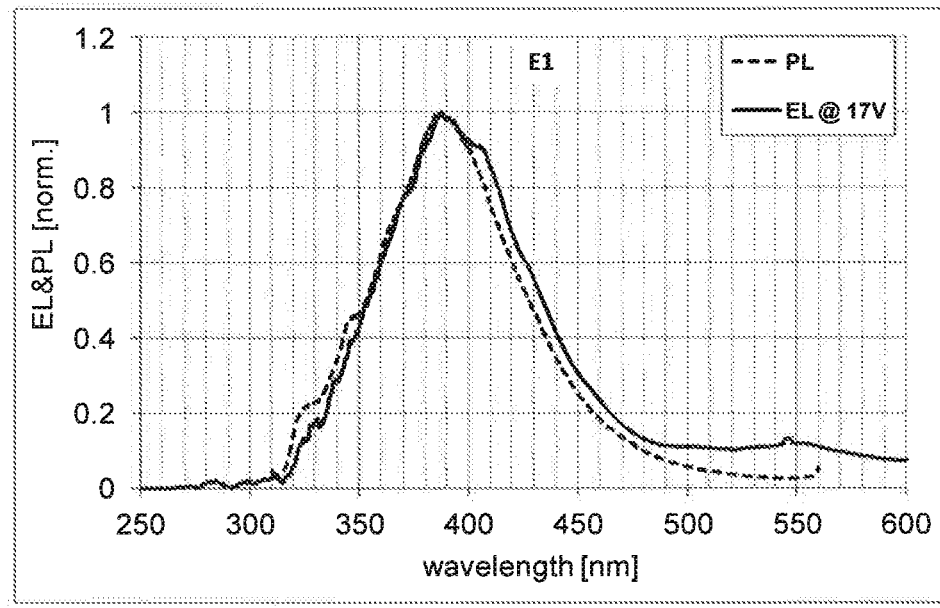
FIGS. 1 to 3 show the electroluminescence (EL) and corresponding photoluminescence (PL) spectra of OLEDs 1 to 3.

The compounds of the formula (1) and (2) can be employed as emitters in the emission layer of organic electroluminescent devices. The choice of the substituents on the rings Ar¹, Ar² and Ar³ can influence the emission here, in particular the emission colour. The person skilled in the art is aware that a broad extension of the conjugated pi-electron system beyond the rings Ar¹, Ar² and Ar³ shifts an emission in the UV region into the visible region. He is also aware that non-aromatic/heteroaromatic substitutions has a lesser influence on the emission colour. On the basis of the technical teaching disclosed herein, the person skilled in the art will be able to select assistance suitable substituents for the emission colour desired in each case. The person skilled in the art knows, for example, that a p-terphenyl radical on compounds of the formula (1) can prevent emission in the UV region, whereas an o-terphenyl or m-terphenyl radical will only influence the emission wavelength in the UV region to a small extent.

It is preferred if the compound of the formula (1) or formula (2), if it is substituted, has a substituent which has 18 conjugated pi electrons or fewer, preferably 14 conjugated pi electrons or fewer and very preferably 10 conjugated pi electrons or fewer.

The groups Ar¹, Ar² and Ar³ are any desired aromatic and/or heteroaromatic rings having 5 or 6 ring atoms.

If the compound of the general formula (1) or (2) is in substituted form, the substituent is preferably the radical defined as R¹ below, with the exception of H.

It is preferred that the groups Ar¹, Ar² and Ar³ in the compound of the formula (1) or (2) each, independently of one another on each occurrence, represent an aromatic or heteroaromatic ring of the general formula (3), where the linking between the groups Ar¹, Ar² and Ar³ can take place at any desired site of the compound of the formula (3):

formula (3)

where the rings Ar¹ and Ar² in formula (1), and the rings Ar¹ and Ar³ or Ar² and Ar³ in formula (2) have two common ring atoms, where, in the case of the formula (2), the rings Ar¹ and Ar² have no common ring atoms; and where the symbols used have the following meanings:

Q is on each occurrence, identically or differently, X=X, NR¹, O, S or Se, preferably Q preferably X=X, NR¹ or S.

X is on each occurrence, identically or differently, CR¹ or N; or, in the case where it is a bridgehead atom, C;

R¹ is, identically or differently on each occurrence, H, D, F, $N(R^2)_2$, CN, $Si(R^2)_3$, $B(OR^2)_2$, $P(R^2)_2$, $S(=O)R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, or CN, or an uncondensed aromatic ring system having 6 to 18 aromatic ring atoms or an uncondensed heteroaromatic ring system having 5 to 18 aromatic ring atoms, each of which may be substituted by one or more radicals $R^2$, or a condensed aromatic or heteroaromatic ring system having 8 to 12 aromatic ring atoms, which may in each case be substituted by one or more radicals $R^2$, or a combination of two or more of these groups, two or more substituents $R^1$ may also form a mono- or polycyclic aliphatic ring system with one another here;

$R^2$ is, identically or differently on each occurrence, H, D, F, $N(R^3)_2$, CN, $Si(R^3)_3$, $B(OR^3)_2$, $P(=O)(R^3)_2$, $P(R^2)_2$, $S(=O)R^3$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms may be replaced by D, F, Cl or CN, or an uncondensed aromatic ring system having 6 to 18 aromatic ring atoms or an uncondensed heteroaromatic ring system having 5 to 18 aromatic ring atoms, each of which may be substituted by one or more radicals $R^3$, or a condensed aromatic or heteroaromatic ring system having 8 to 12 aromatic ring atoms, which may in each case be substituted by one or more radicals $R^2$, or a combination of two or more of these groups; two or more adjacent radicals $R^2$ may form a mono- or polycyclic aliphatic ring system with one another here;

$R^3$ is, identically or differently on each occurrence, H, D, F, a straight-chain alkyl, alkoxy or thioalkoxy group having 1 to 40 C atoms or a branched or cyclic alkyl, alkoxy or thioalkoxy group having 3 to 40 C atoms, an aromatic ring system having 6 to 12 aromatic ring atoms or a heteroaromatic ring system having 5 to 12 aromatic ring atoms, in which, in addition, one or more H atoms may be replaced by F; two or more substituents $R^3$ may also form a mono- or polycyclic aliphatic ring system with one another here;

The compound of the formula (1) or (2) is preferably one of the following formulae (4) to (12).

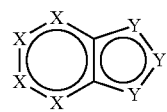

formula (4)

formula (5)

formula (6)

formula (7)
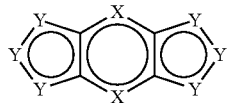

formula (8)
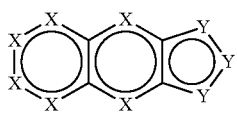

formula (9)
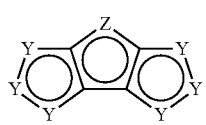

formula (10)
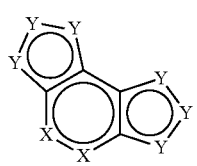

formula (11)
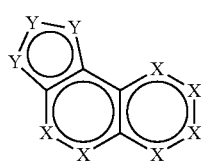

formula (12)
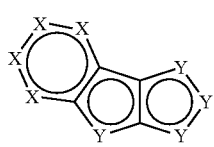

where the symbols used have the following meanings:

X is on each occurrence, independently of one another, $CR^1$ or N;

Y is on each occurrence, independently of one another, $CR^1$, N, $NR^1$, S or O; with the proviso that at least one Y in each of the 5-membered rings is $NR^1$, S or O;

Z is on each occurrence, independently of one another, $NR^1$, O or S;

where $R^1$ has the same meaning as defined above.

It is furthermore preferred that the groups $Ar^1$, $Ar^2$ and $Ar^3$ in the compound of the formula (1) or (2) are, identically or differently on each occurrence, one of the following groups, where the bonding between the groups may take place at any desired and chemically possible site, and where the groups may be substituted by one or more radicals $R^1$, which are independent of one another, where the radicals $R^1$ are defined as indicated above.

formula (13)

formula (14)

formula (15)

formula (16)

formula (17)

formula (18)

formula (19)

formula (20)

formula (21)

formula (22)

formula (23)

formula (24)

formula (25)

The compound of the formula (1) or (2) is preferably a fluorescent emitter compound, i.e. the compound emits radiation from the electronically excited singlet state. The compound of the formula (1) or (2) is preferably employed as UV light-emitting compound, i.e. the electroluminescent device according to the invention is preferably a UV light-emitting device.

The compound of the general formula (1) or (2) is preferably one of the following compounds:

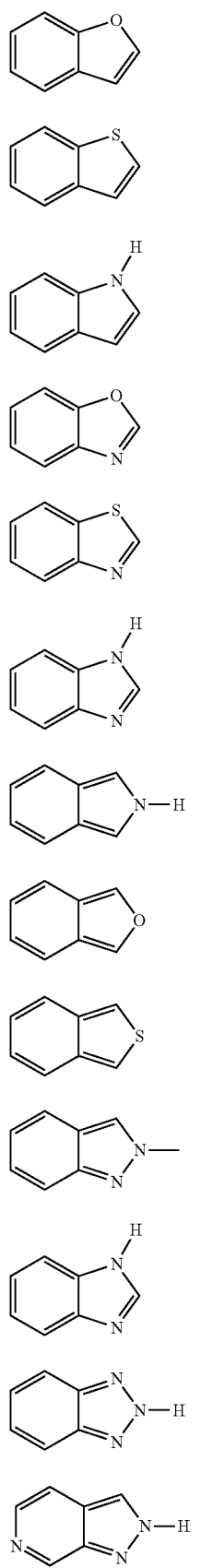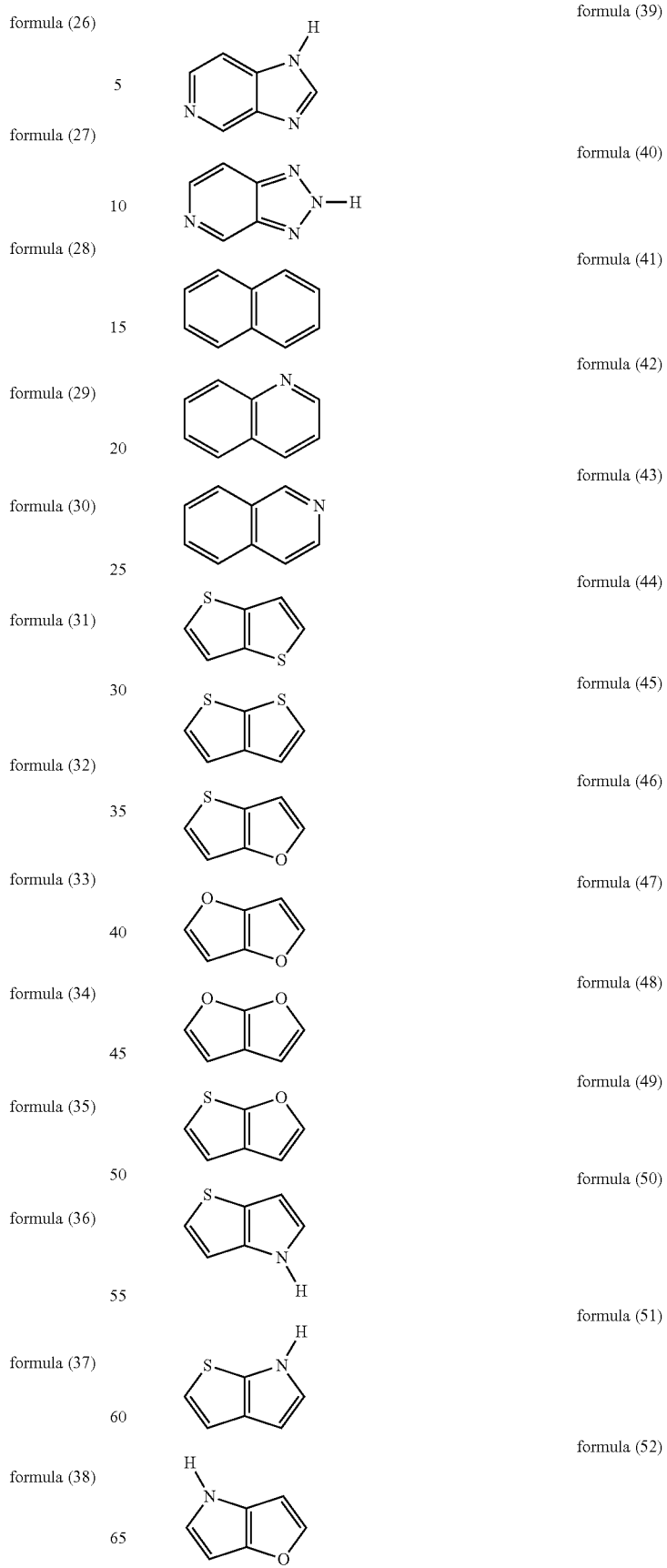

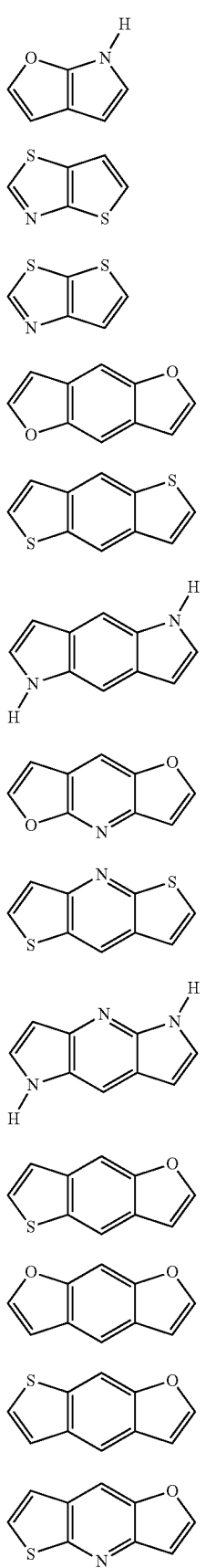

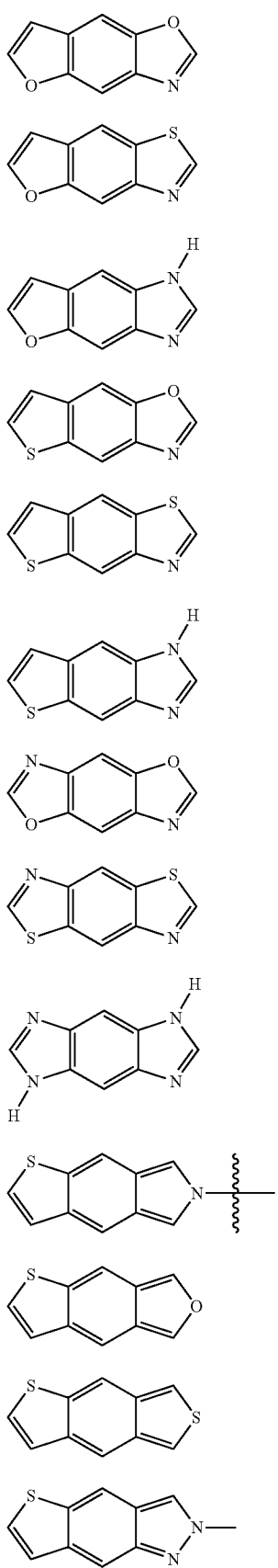

-continued
formula (100) 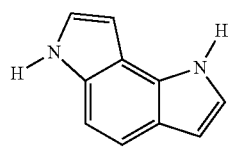
formula (101) 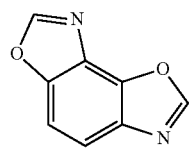
formula (102) 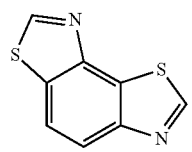
formula (103) 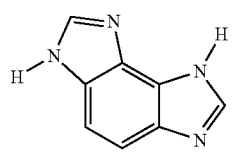
formula (104) 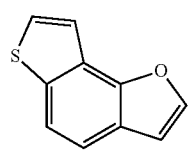
formula (105) 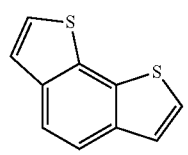
formula (106) 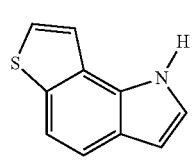
formula (107) 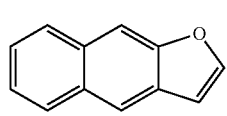
formula (108) 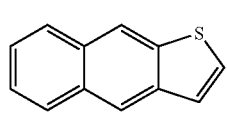
formula (109) 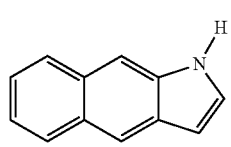
formula (110) 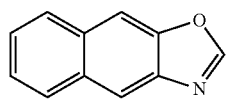
formula (111) 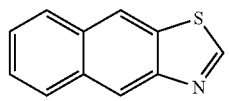
formula (112) 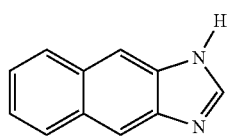
formula (113) 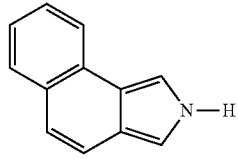
formula (114) 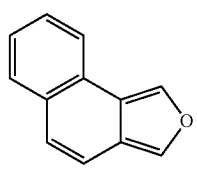
formula (115) 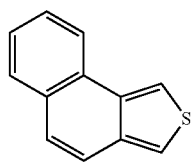
formula (116) 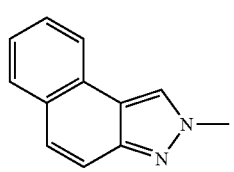
formula (117) 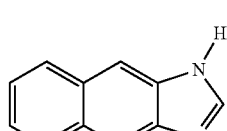
formula (118) 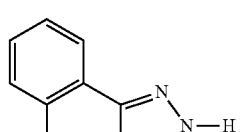
formula (119) 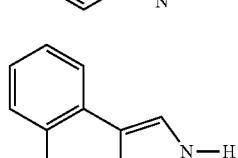
formula (120) 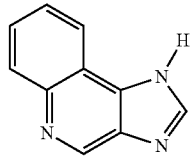

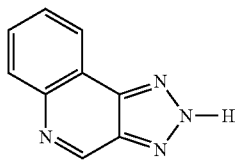
formula (121)

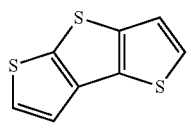
formula (122)

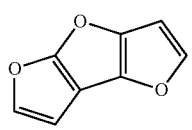
formula (123)

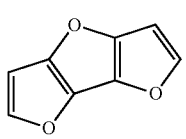
formula (124)

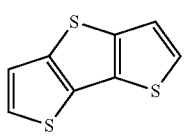
formula (125)

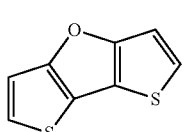
formula (126)

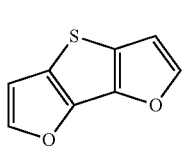
formula (127)

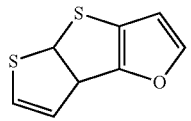
formula (128)

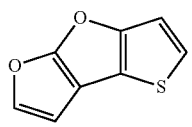
formula (129)

where one or more H atoms of these compounds may be replaced by a radical R¹, which is defined as above, but in this case is other than H.

The compounds of the formula (1) or (2) preferably contain one, two, three or four of the radicals R¹, but preferably one or two radicals R¹, which are other than H.

It is furthermore preferred that the compound of the general formula (1) is one of the following compounds:

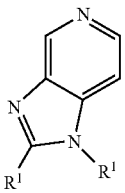
formula (130)

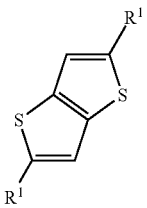
formula (131)

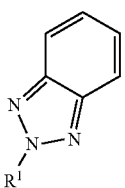
formula (132)

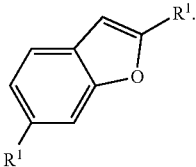
formula (133)

In a furthermore preferred embodiment, the radical R¹ in the compound of the formula (1) or (2) of the electroluminescent device according to the invention is selected, identically or differently on each occurrence, from the group which of H, D, F, CN, a straight-chain alkyl, alkoxy or thioalkoxy group having 1 to 40 C atoms or a branched or cyclic alkyl, alkoxy, alkylalkoxy or thioalkoxy group having 3 to 20 C atoms, each of which may be substituted by one or more radicals R², or an uncondensed aromatic or heteroaromatic ring system having 5 to 18 aromatic ring atoms, which may in each case be substituted by one or more radicals R², or a condensed aromatic or heteroaromatic ring system having 8 to 12 aromatic ring atoms, which may in each case be substituted by one or more radicals R². More preferably, R¹ is equal to H, a straight-chain alkyl or alkoxy group having 1 to 12 C atoms or an aromatic ring system having 6 to 10 aromatic ring atoms, each of which may be substituted by one or more radicals R².

The group R² is preferably, identically or differently on each occurrence, F or a straight-chain alkyl or alkoxy group having 1 to 12 C atoms.

In a further embodiment, the compound of the formula (1) or (2) of the electroluminescent device according to the invention is one of the following compounds:

formula (134)

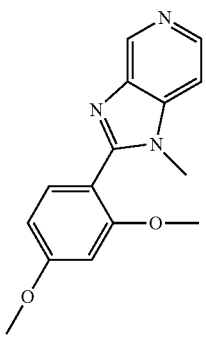

formula (135)

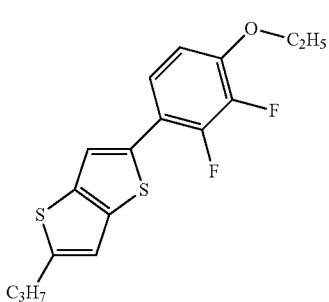

formula (136)

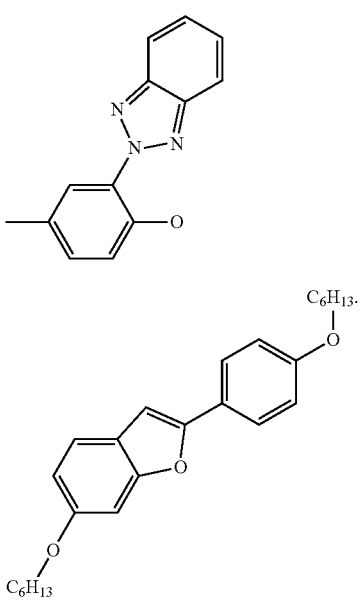

formula (137)

or with at least one emitter of the formula (1) or (2). The present invention therefore also relates to an electroluminescent device which is characterised in that the emission layer comprises at least one compound of the formula (1) or (2) as host material in the emission layer.

The present invention therefore also relates to an electroluminescent device which is characterised in that the emission layer comprises at least one compound of the formula (1) or (2) as host material and at least one compound of the formula (1) or (2) as emitter in the emission layer.

Preference is furthermore given for the purposes of the present invention to the use of polystyrene or of derivatives of polystyrene as host material.

In a further embodiment, the emitting layer comprises at least one further UV emitter and/or at least one further host material.

Suitable materials for the emitting layer, either as emitter or as host, are compiled by way of example in the following table with the corresponding references.

formula (138)

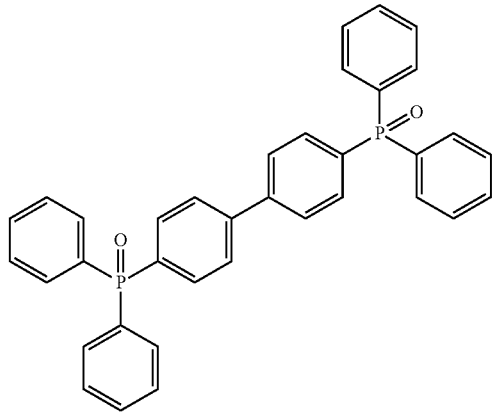

Burrows et al., Appl. Phys. Lett., 88, 183503, 2006 formula (139)

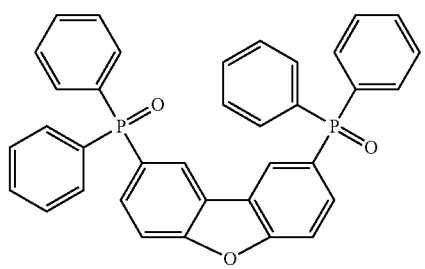

Vecchi et al,. Organic Letters, 8
4211, 2006

In an embodiment, the emitting layer of the device according to the invention comprises an emitter of the formula (1) or (2) and at least one host material. The host material here has a larger band gap (=separation between valence band (LUMO—lowest unoccupied molecular orbital) and conduction band (HOMO—highest occupied molecular orbital)) or a higher excited electronic state. The host material consequently has a higher $S_1$ or $T_1$ level, preferably the $S_1$ level of the host material is higher than that of the emitter. $S_1$ here is the first electronically excited singlet level. $T_1$ is the first electronically excited triplet level.

The above-mentioned materials can be employed as emitters in the emission layer. However, the materials of the formula (1) or (2) can also be employed as host materials. The host compound of the formula (1) or (2) can be doped either with at least one dopant (emitter) of any desired type formula (140)
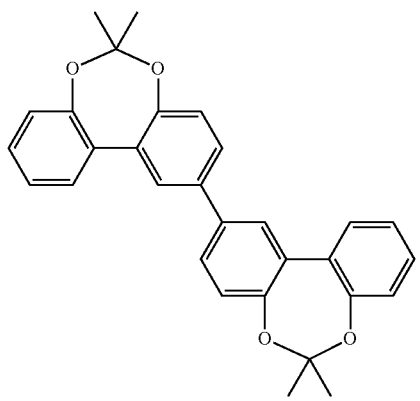
Zhang et al., J. Phys. Chem. B, 108, 9571, 2004
formula (141)
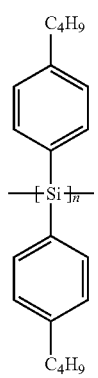
Hoshino et al., J. Appl. Phys., 88, 2892, 2000
formula (142)
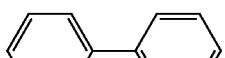
Zou et al., Appl. Phys. Lett., 79, 2282, 2001
formula (143)
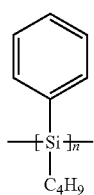
Sharma et al., Appl. Phys. Lett., 88, 143511, 2006
formula (144)
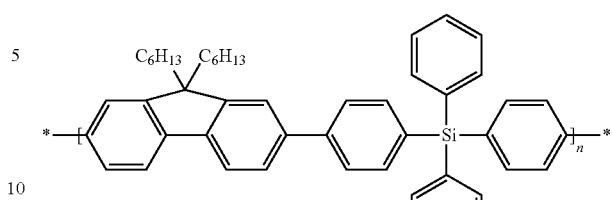
Zhou et al., Macromolecules, 40, 3015, 2007
formula (145)
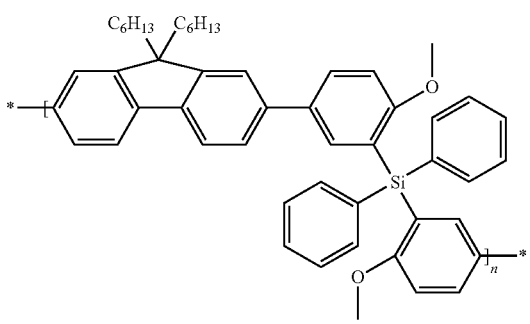
Zhou et al., Macromolecules, 40, 3015, 2007
formula (146)
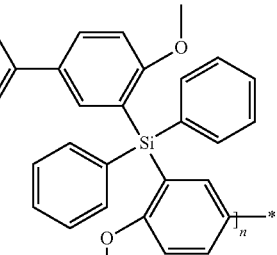
Zhou et al., Macromolecules, 40, 3015, 2007
formula (147)
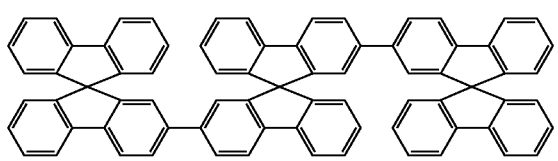
Wong et al., Organic Letters, 7, 5131, 2005 formula (148)
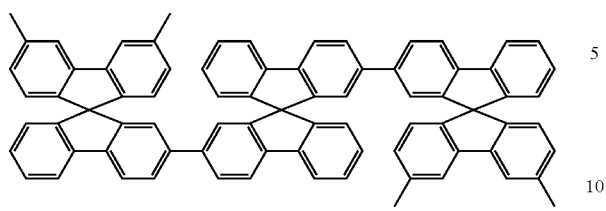
Wong et al., Organic Letters, 7, 5131, 2005
formula (149)
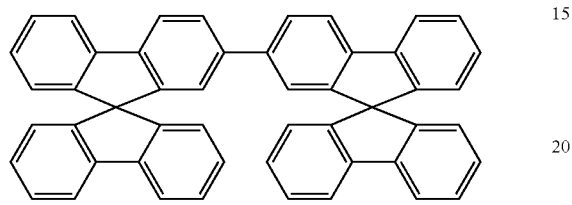
Chao et al., Adv. Mater., 17, 992, 2005
formula (150)
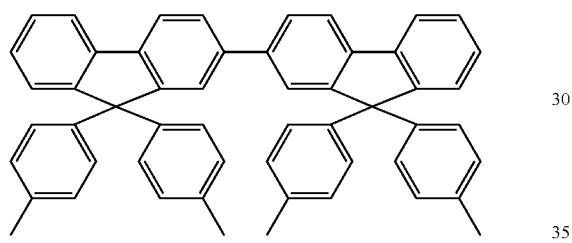
Chao et al., Adv. Mater., 17, 992, 2005
formula (151)
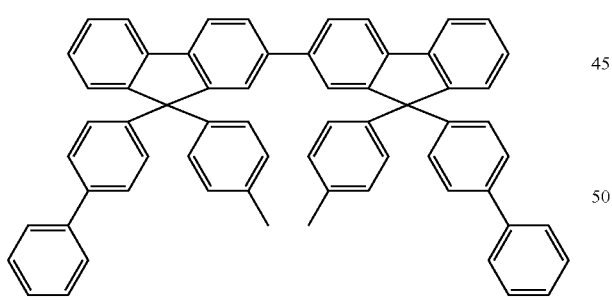
Chao et al., Adv. Mater., 17, 992, 2005
formula (152)
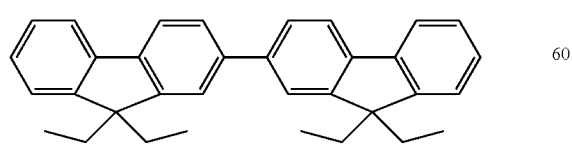
Chao et al., Adv. Mater., 17, 992, 2005
formula (153)
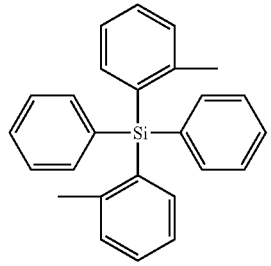
Ren et al., Chem. Mater., 16, 4743, 2004
formula (154)
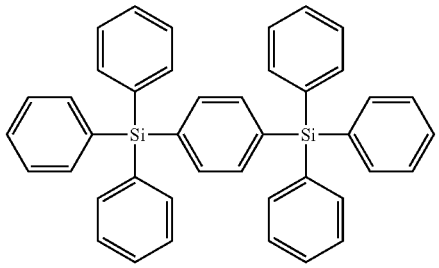
Ren et al., Chem. Mater., 16, 4743, 2004
formula (155)
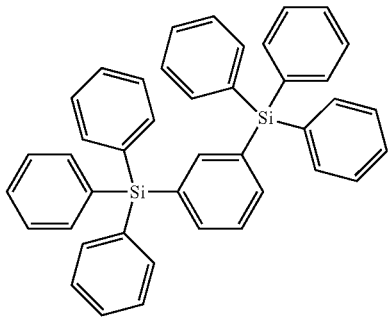
Ren et al., Chem. Mater., 16, 4743, 2004
formula (156)
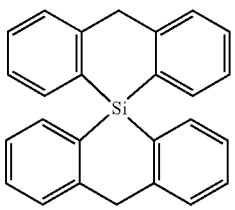
Ren et al., Chem. Mater., 16, 4743, 2004
formula (157)
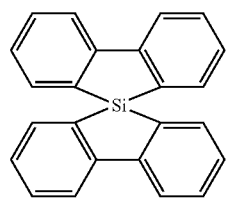
Ren et al., Chem. Mater., 16, 4743, 2004 formula (158)
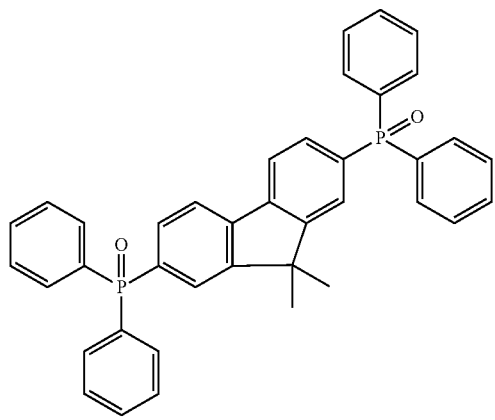
Padmaperuma et al., Chem. Mater., 18, 2389, 2006
formula (159)
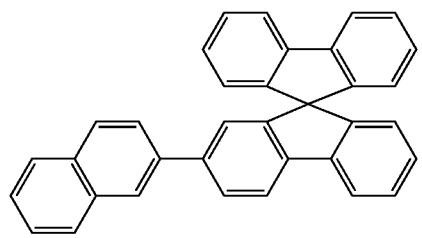
Etori et al., Jpn. J. Appl. Phys., 46, 5071, 2007
formula (160)
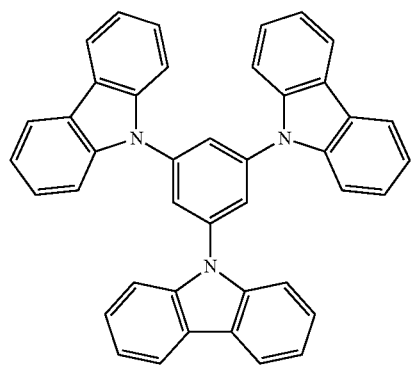
Etori et al., Jpn. J. Appl. Phys., 46, 5071, 2007
formula (161)
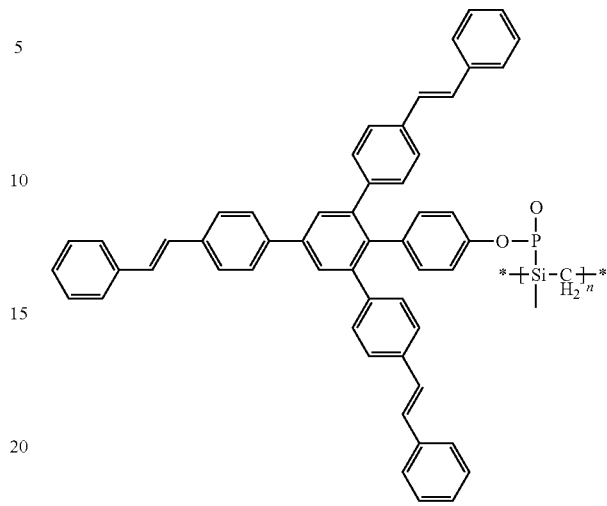
Spiliopoulos et al., Macromolecules, 35, 7254, 2002
formula (162)
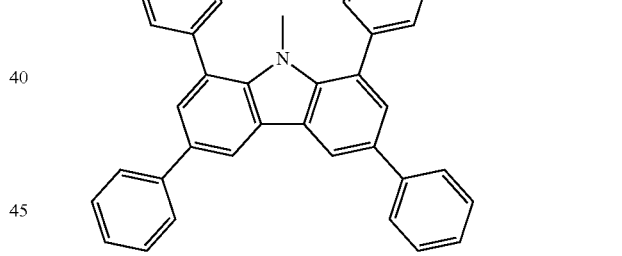
Ichikawa et al., Thin Solid Films, 515, 3932, 2007
formula (163)
Niu et al., RSC Adv., 1, 415, 2011
formula (164)
Niu et al., RSC Adv., 1, 415, 2011

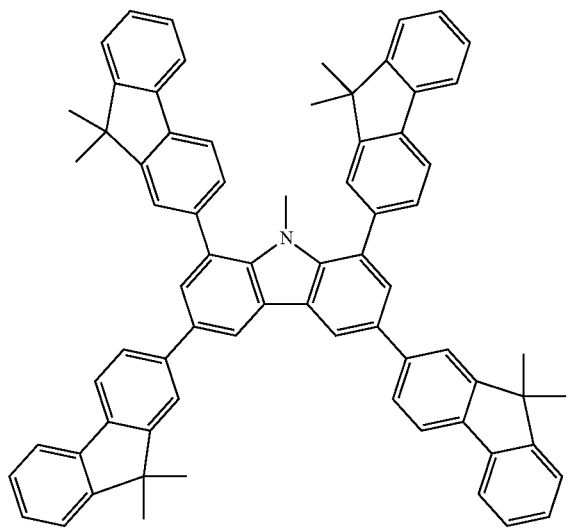

Niu et al., RSC Adv., 1, 415, 2011 formula (166)

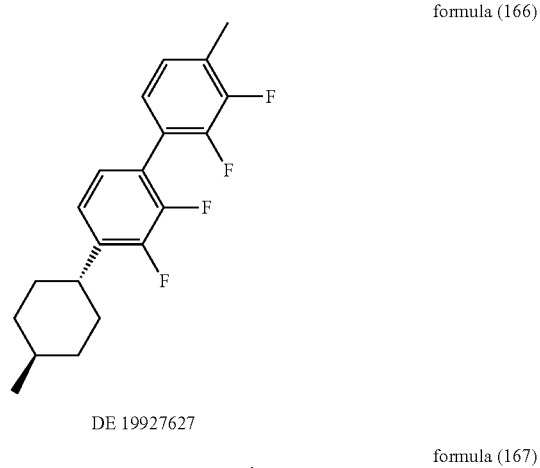

DE 19927627 formula (167)

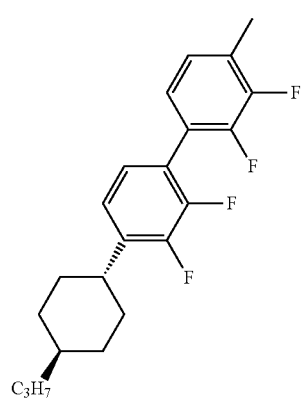

DE 19927627

In an embodiment, the emitting layer of the device according to the invention comprises an emitter of one or more of the formulae (130) to (137); preferably formulae (134) to (137), and at least one host material.

The preferred host material in the emitting layer of the device according to the invention is a compound of the formula (166) or (167).

In an embodiment, the emitting layer of the device according to the invention comprises an emitter of one or more of the formulae (130) to (137); preferably formulae (134) to (137), and at least one host material of formula (166) or (167).

In an embodiment, the emitting layer of the device according to the invention comprises an emitter of one or more of the formulae (130) to (137), preferably of the formulae (134) to (137), and at least one host material of formula (166) or (167) or polystyrene.

In an embodiment, the emitting layer of the device according to the invention comprises an emitter of formulae (134 to (137), and, as host materials, the compounds of the formulae (166) and (167) and polystyrene.

The amount of the compound of the formula (1) or (2) in the emitting layer is preferably in the range from 1 to 60% by weight, more preferably 5 to 35% by weight, based on the total weight of all constituents of the emitting layer.

The amount of the host material in the emitting layer is preferably in the range from 40 to 99% by weight, more preferably 65 to 95% by weight, based on the total weight of all constituents of the emitting layer.

The performance data of the devices according to the invention can be improved further in various ways.

As already mentioned, at least one host material is usually used in the emission layer of organic electroluminescent devices besides the emitter or emitters. However, particularly good results can be achieved on use of a mixed-host system in the device according to the invention.

In a further preferred embodiment, a mixed host is used in the emission layer of the device according to the invention. This enables the radiation intensities of the devices to be significantly increased and the operating voltages to be significantly reduced. Mixed host means that the host consists of at least 2 different compounds. The mixed host preferably comprises at least one compound of one of the formulae (138) to (167), more preferably a compound of one of the formulae (166) or (167). In addition, the mixed host comprises a further host compound of any desired type. The person skilled in the art will be able to fall back here without difficulties on a multiplicity of host compounds known in the prior art.

In a further embodiment, further layers are introduced between the emitting layer and one of the two electrodes.

It is advantageous if at least one blocking layer is used between emitting layer and one of the electrodes. This enables, in particular, the operating voltage to be reduced and the absolute radiation intensities to be increased. Suitable blocking layers can block excitons, electrons or holes.

The present invention therefore also relates to a device, as disclosed herein, which comprises a further layer between the emitting layer and one of the two electrodes, characterised in that the additional layer comprises an exciton-blocking material (blocking material) having a band gap of 3.4 eV or higher, preferably 3.6 eV or higher, very preferably 3.8 eV or higher and very particularly preferably 4.0 eV or higher.

The present invention also relates to a device, as disclosed herein, which comprises a further layer between the emitting layer and one of the two electrodes, characterised in that the additional layer comprises a hole-blocking material (barrier material) having an HOMO of lower than −5.9 eV, preferably lower than −6.0 eV, very preferably lower than −6.2 eV and very particularly preferably lower than −6.3 eV.

The present invention also relates to a device, as disclosed herein, which comprises a further layer between the emitting layer and one of the two electrodes, characterised in that the additional layer comprises an electron-blocking material (blocking material) having an LUMO of higher than −2.2 eV, preferably higher than −2.1 eV.

In a very preferred embodiment, the device according to the invention comprises a blocking layer which blocks both excitons and also holes.

In a further very preferred embodiment, the device according to the invention comprises a blocking layer which blocks both excitons and also electrons.

In a very preferred embodiment, the blocking layer is formed by crosslinking one or more compounds containing at least 2 or more crosslinkable group (hereafter precursor). Especial preference is given to a blocking layer which is formed by precursors of the compound of the formula (1) or (2), which furthermore contain at least 2 or more crosslinkable groups.

A crosslinkable group is a group containing a crosslinkable reagent which results in a crosslinking reaction with the aid of heat, radiation or both. The radiation source can be an electron beam and UV radiation. The preferred UV radiation source emits radiation of a wavelength of 200 to 400 nm, very preferably a radiation of 300 to 400 nm. Suitable sources for UV radiation are, for example, mercury UV fluorescent lamps, UV LEDs and UV laser diodes.

Suitable crosslinkable groups are, for example, the acrylate group (for example Scheler et al., In Macromol, Symp. 254, 203-209 (2007)), the vinyl or styrene group (for example WO 2006/043087) and the oxetane group (for example Mueller et al., In Nature 421, 829-833 (2003)).

In a preferred embodiment, the precursor compound for the blocking layer is a compound of the general formula (168).

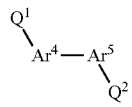

formula (168)

where $Ar^4$ and $Ar^5$ each, independently of one another, denote an aromatic or heteroaromatic 5- or membered ring and preferably represent a ring of the formula (3) defined above, and $Q^1$ and $Q^2$ is each, independently of one another, a crosslinkable group, which is preferably selected from the following formula (169) to (192):

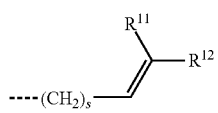

formula (169)

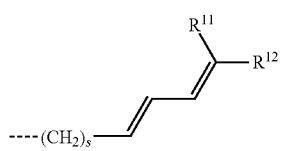

formula (170)

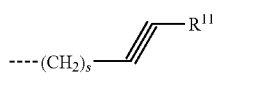

formula (171)

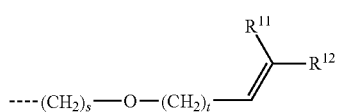

formula (172)

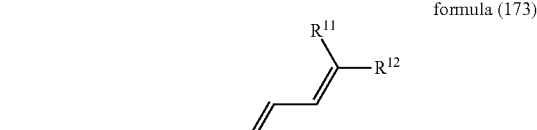

formula (173)

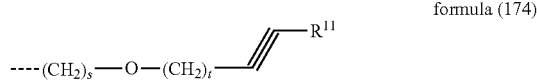

formula (174)

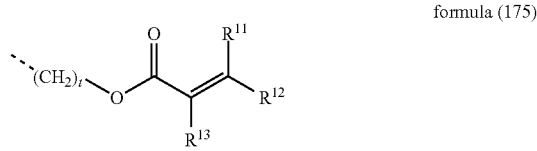

formula (175)

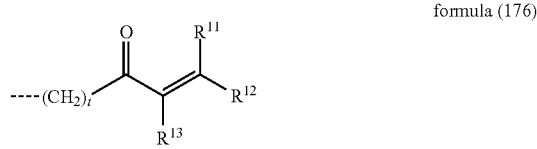

formula (176)

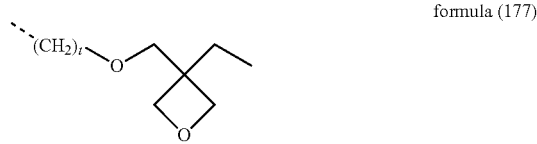

formula (177)

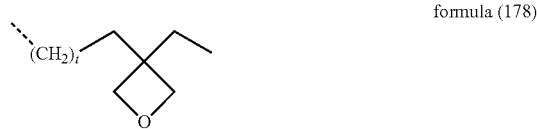

formula (178)

formula (179)

formula (180)

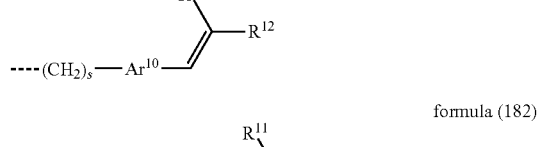

formula (181)

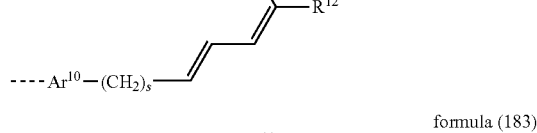

formula (182)

formula (183)

formula (184)

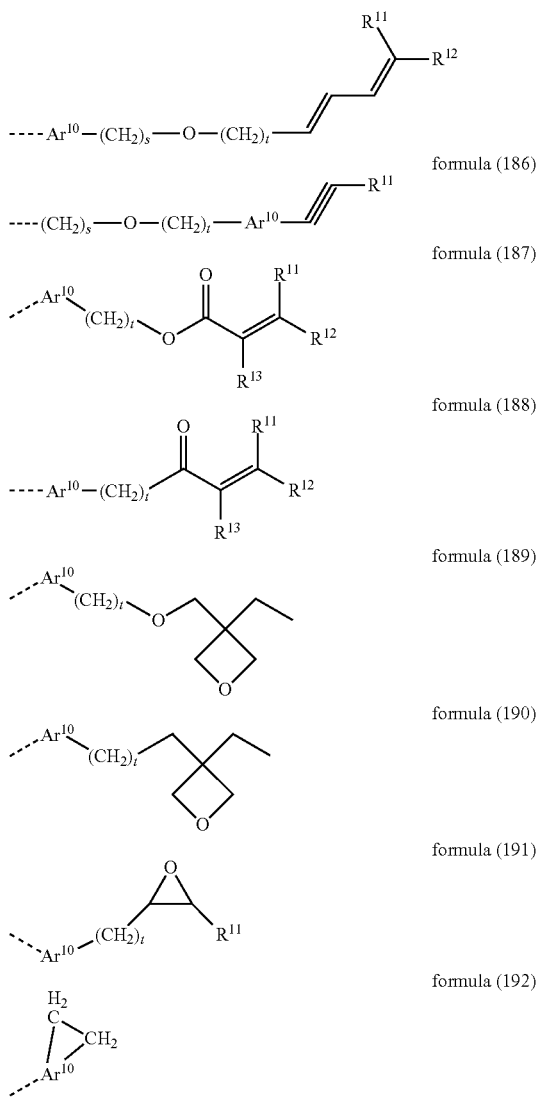

formula (185)

formula (186)

formula (187)

formula (188)

formula (189)

formula (190)

formula (191)

formula (192)

where
the radicals $R^{11}$, $R^{12}$ and $R^{13}$ are on each occurrence, identically or differently, H, a straight-chain or branched alkyl group having 1 to 6 C atoms;
$Ar^{10}$ in the formulae (181) to (192) is a mono- or polycyclic, aromatic or heteroaromatic ring system having 5 or 6 ring atoms, which may be substituted by one or more radicals R, where R is on each occurrence, identically or differently, H, D, F, an aliphatic hydrocarbon radical having 1 to 20 C atoms, an aromatic hydrocarbon radical having 6 to 20 aromatic ring atoms or a heteroaromatic hydrocarbon radical having 5 to 20 aromatic ring atoms, in which, in addition, one or more H atoms may be replaced by F; where two or more substituents R may also form a mono- or polycyclic, aliphatic or aromatic ring system with one another;
s is an integer from 0 to 8;
t is an integer from 1 to 8;
and where the dashed bond represent the linking of the crosslinkable group to one of the mono- or polycyclic, aromatic or heteroaromatic ring systems $Ar^4$ or $Ar^5$ in formula (168).

In the group of the formula (180), the two dashed lines mean that $Ar^4$ and/or $Ar^5$ in the compound of the formula (168) are connected in the ortho position to the two carbon atoms of the ethylene group, so that a four-membered ring forms. Analogously, $Ar^{10}$ in the group of the formula (192) is connected to the two carbon atoms of the ethylene group in the ortho position, so that a four-membered ring forms.

Examples of preferred precursor compounds for the blocking layer in accordance with the embodiments indicated above are the compounds of the following structures.

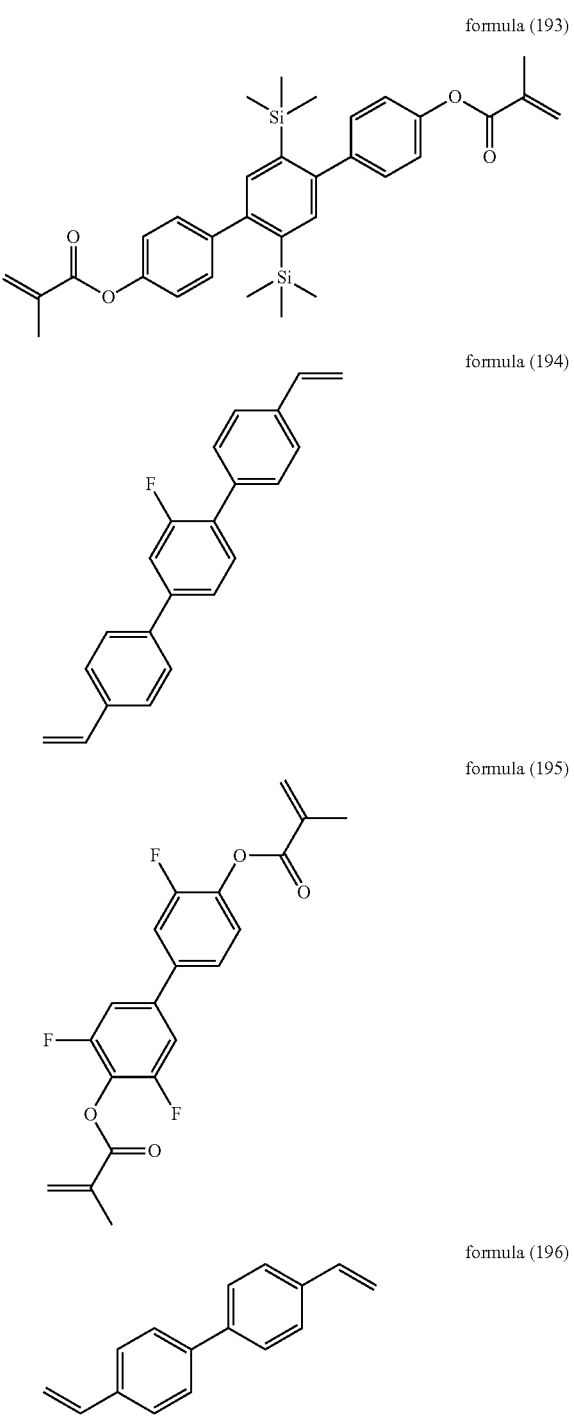

formula (193)

formula (194)

formula (195)

formula (196)

-continued
formula (197)
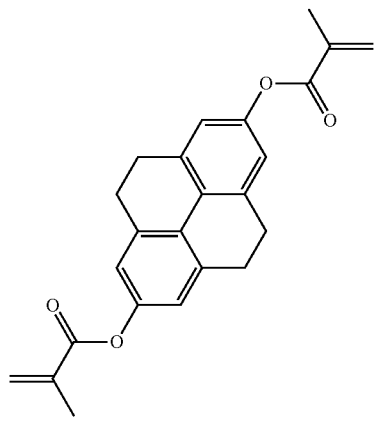
formula (198)
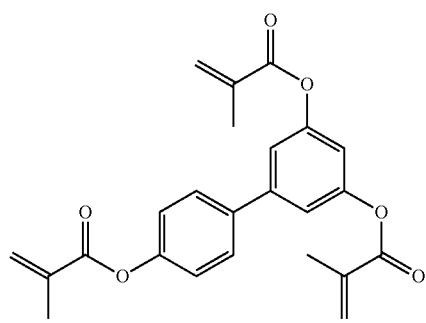
formula (199)
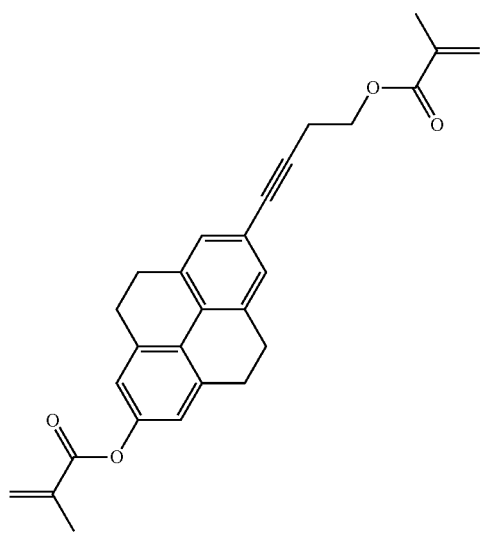
-continued
formula (200)
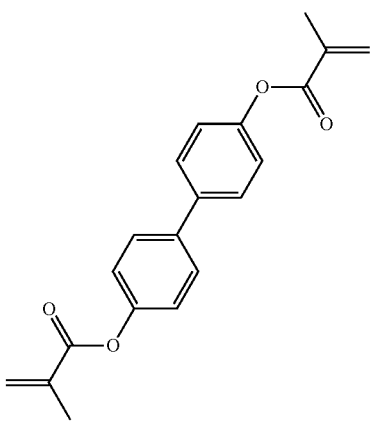
formula (201)
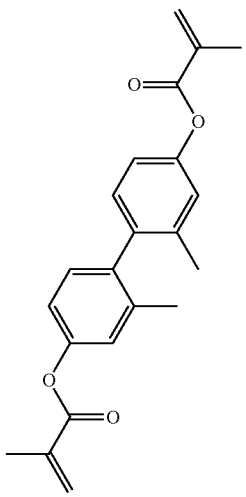
formula (202)
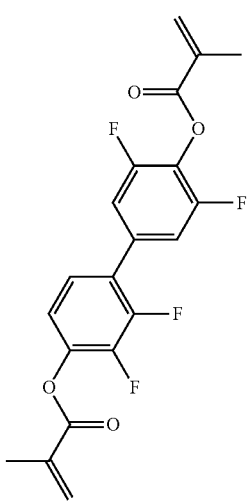

formula (203)
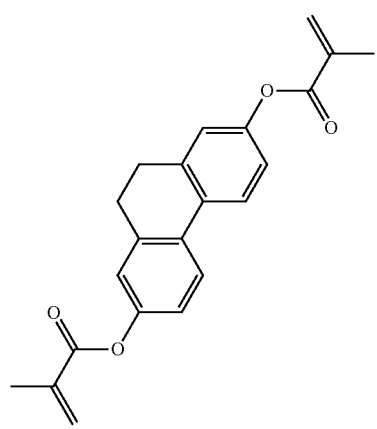
formula (204)
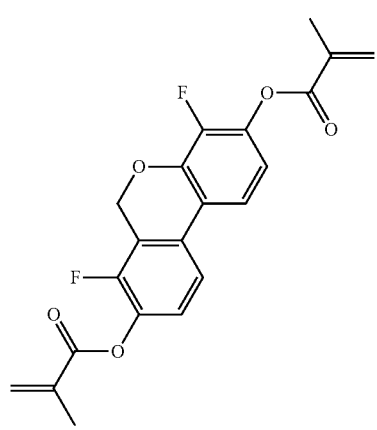
formula (205)
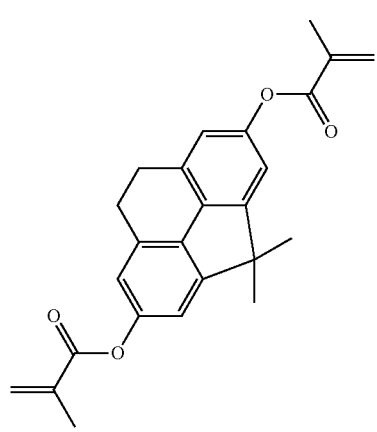
formula (206)
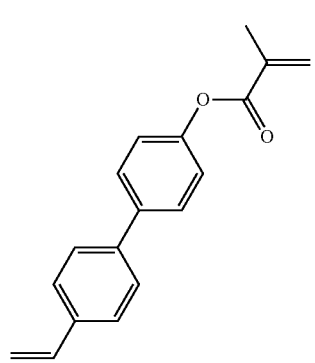
formula (207)
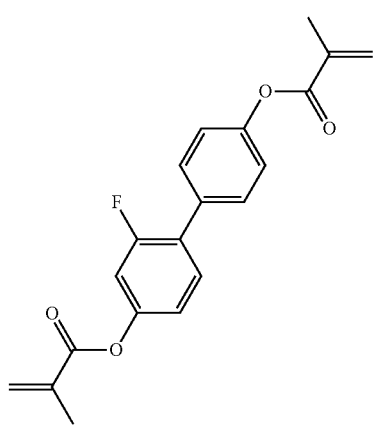
formula (208)
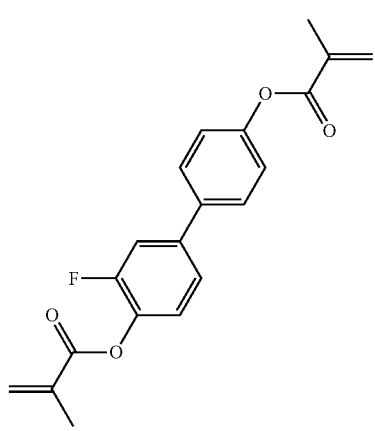
formula (209)
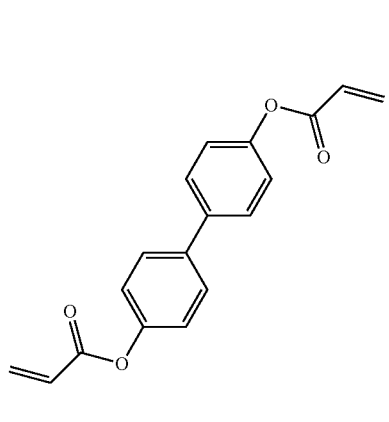
formula (210)
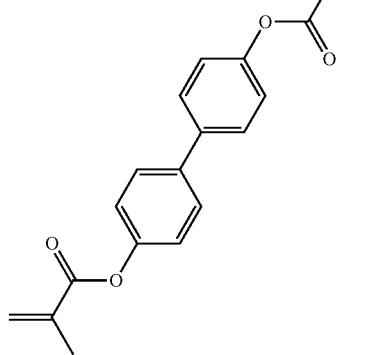

formula (211)

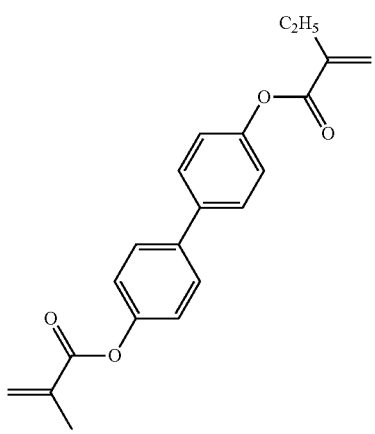

formula (212)

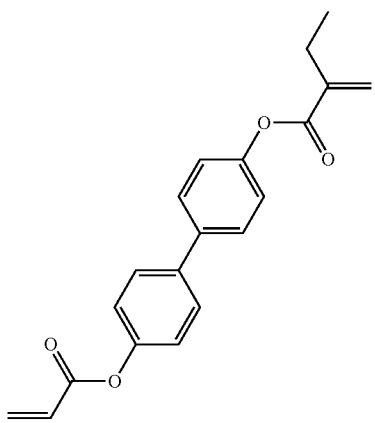

formula (213)

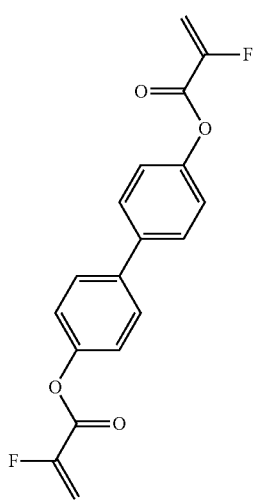

formula (214)

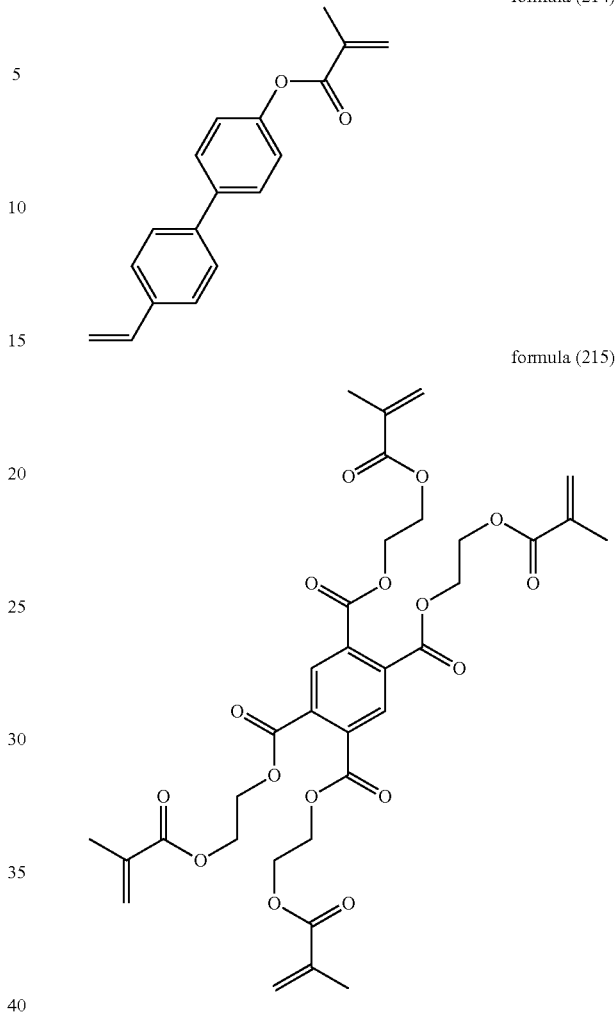

formula (215)

Processes for the preparation of the said precursor compounds are well known to the person skilled in the art from the prior art (for example WO 2010/133278 and U.S. Pat. No. 7,807,068).

In a furthermore preferred embodiment, the electroluminescent device according to the invention emits radiation having a wavelength in the range from 280 nm and 380 nm.

The electroluminescent device can be any electroluminescent device. The person skilled in the art will be able to make a selection here without difficulties from a large number of devices known to him. The electroluminescent device is preferably an organic light-emitting diode (OLED), polymeric light-emitting diode (PLED), organic light-emitting electrochemical cell (OLEC, LEC or LEEC), an organic light-emitting transistor (O-LETs) and an organic light-emitting electrochemical transistor. In a very preferred embodiment, the present invention relates to OLEDs or PLEDs. In a furthermore very preferred embodiment, the present invention relates to OLECs.

The electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. Interlayers, which have, for example, an exciton-blocking function, may likewise be introduced between two emitting layers. However, it should be pointed out that each of these layers does not necessarily have to be present. The electroluminescent device may comprise one emitting layer, or it may comprise a plurality of emitting layers, where it is preferred if it comprises one emitting layer.

In a preferred embodiment, the electroluminescent device according to the invention comprises a hole-injection layer, which is also called buffer layer. The work function of the hole-injection layer is greater than 5.0 eV, preferably greater than 5.4 eV, very preferably greater than 5.8 eV and very particularly preferably greater than 6.0 eV. In a further embodiment, the hole-injection layer comprises conductive, conjugated polymers, such as, for example, polythiophene, polyaniline and polypyrrole and derivatives thereof. Such polymers are in some cases also commercially available, such as, for example, CLEVIOS™ P VP Al 4083, CLEVIOS™ HIL 1.3, and CLEVIOS™ HIL 1.3N from Heraeus Precious Metals GmbH & Co. KG.

The compounds of the formula (1) or (2) may also be incorporated into the side chain of polymers. The incorporation of the compounds into the side chain of polymers has various advantages, which are shown below.
1) The polymers have improved solubility in organic solvents and thus also improved processability.
2) The polymers have improved layer-formation properties,
3) The polymers have higher glass transition temperatures (Tg) compared with small molecules.
4) The polymers have a broader process window and improved performance data.

The invention therefore also relates to a polymer of the general formula (216)

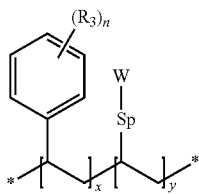

formula (216)

where the following applies to the indices and symbols used:
Sp is a single bond or a non-conjugated spacer;
W is, identically or differently on each occurrence, a structural unit of the formula (1) or (2) as defined above, where the bonding between Sp and the compound of the formula (1) or (2) can take place at any desired and chemically possible position;
x is a number between 0 and 80 mol %;
y is a number from 2 to 100 mol %, where x+y=100 mol %;
n is an integer from 0 to 5; and
$R^1$ is defined exactly as indicated above for $R^1$;

The polymer according to the invention preferably has a photoluminescence and/or electroluminescence emission in the wavelength range from 280 and 380 nm.

In a further preferred embodiment of the present invention, the polymer according to the invention emits both radiation in the wavelength range from 280 to 380 nm and also radiation in the wavelength range from 400 to 500 nm.

In a preferred embodiment, the spacer is a hydrocarbon radical having 1 to 20 C atoms, where alkyl and alkylalkoxy radicals are preferred.

In a very particularly preferred embodiment, the polymer is one of the following general compounds.

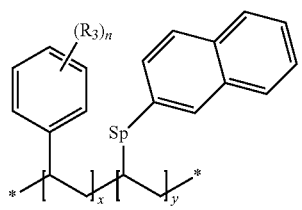

formula (217)

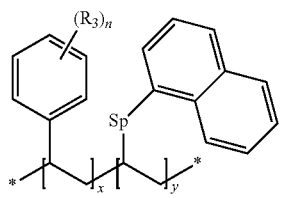

formula (218)

where $R^3$ is defined as in formula (216).

In a preferred embodiment, Sp in the polymer according to the invention is a single bond. It is very preferred if the aromatic or heteroaromatic ring is of W are bonded directly to the polymer backbone. In a particularly preferred embodiment, this is the case in the polymers of the formulae (217) and (218).

In a preferred embodiment, x is equal to 0 mol-% and y is equal to 100 mol-% in the polymer according to the invention. This applies, in particular, in an embodiment in which the polymer is one of the formulae (217) and (218).

The following general synthetic procedure can be used for the preparation of polymers of the formula (216):
Free-radical polymerisation for polymers of the formula (216)

The monomers are weighed out in the desired ratio into a flask and carefully rendered inert. 10 equivalents of toluene relative to the total amount of monomer are added, and the solution is rendered inert again. In a second flask, 0.01 equivalents of AIBN relative to the total amount of monomer are weighed out and dissolved in ten times the molar amount of toluene with gentle warming. The monomer solution is heated to 70° C., and one percent of the toluene/AIBN solution is added rapidly by means of a syringe. The solution is stirred at 70° C. for 72 hours with exclusion of light, then cooled to room temperature and stirred for a further 24 hours. The polymer is precipitated twice from toluene in ethanol, filtered off and dried in a high vacuum for 24 hours.

The invention furthermore relates to a formulation comprising at least one polymer according to the invention and at least one solvent.

The invention also relates to a composition comprising at least one polymer according to the invention and at least one organic functional material or an organic semiconductor, as described below.

The invention furthermore relates to an electroluminescent device comprising at least one of the polymers according to the invention. The preferred electroluminescent devices here are the devices described above, where the OLEDs/PLEDs and OLECs are also very particularly preferred here.

The present invention also relates to compositions comprising at least one of the compounds of the formula (1) or (2) or at least one polymer of the general formula (216) and at least one organically functional material or an organic semiconductor selected from the group of the emitters, host materials, matrix materials, electron-transport materials (ETM), electron-injection materials (EIM), hole-transport materials (HTM), hole-injection materials (HIM), electron-blocking materials (EBM), hole-blocking materials (HBM), exciton-blocking materials (ExBM). The emitters here can be both fluorescent and phosphorescent emitters. The person skilled in the art will be able to make a selection here without difficulties from a multiplicity of known organic functional materials having the said functions. The definitions and examples of various organic functional materials can be obtained, for example, from the disclosure content of WO 2011/015265.

For the purposes of the present invention, the composition according to the invention preferably comprises at least one host material as organically functional material besides at least one compound of the formula (1) or (2) or at least one polymer of the formula (216) as emitter. The composition very preferably comprises two host materials besides the at least one compound of the formula (1) or (2) or besides the at least one polymer of the formula (216) as emitter. The composition very particularly preferably comprises precisely one compound of the formula (1) or (2) or precisely one polymer of the formula (216) as emitter and two host materials. The composition furthermore very particularly preferably comprises precisely one compound of the formula (1) or (2) or polymer of the formula (216) as emitter and precisely one host material.

The concentration of emitter(s) in the composition is 1 to 60% by weight, and preferably 5 to 35% by weight. The total concentration of the host or host or host materials is 40 to 99% by weight and preferably 40 to 95% by weight.

The devices according to the invention can be produced by various processes. One or more of the layers of the electroluminescent device can be applied by means of a sublimation process, in which the materials are applied by vapour deposition in vacuum sublimation units at an initial pressure less than $10^{-5}$ mbar, preferably less than $10^{-6}$ mbar. However, it is also possible for the initial pressure to be even lower, for example less than $10^{-7}$ mbar.

A preferred process for the application of one or more layers of the electroluminescent device is the OVPD process (organic vapour phase deposition) or a process with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

One or more of the layers of the electroluminescent device can also be applied from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. These processes are also suitable for the application of layers comprising oligomers, dendrimers and polymers.

Likewise possible are hybrid processes, in which, for example, one or more layers are applied from solution and one or more other layers are applied by vacuum vapour deposition.

The present invention therefore also relates to a process for the production of the electroluminescent devices according to the invention by means of sublimation processes and/or by means of processes from solution.

The present invention furthermore relates to a formulation comprising a composition according to the invention and one or more solvents.

Suitable and preferred solvents are, for example, toluene, anisole, xylene, methyl benzoate, dimethylanisole, trimethylbenzene, tetralin, veratrol, tetra-hydrofuran, chlorobenzene or dichlorobenzene and mixtures thereof.

Electroluminescent devices which emit blue light and/or UV radiation can be employed in a versatile manner. Applications which require light or radiation having very short wavelengths and thus represent areas of application for the devices according to the invention are found, for example, in the area of life science and medicine (for example for cell imaging) or in the area of biosensors. The devices according to the invention are furthermore used in the electronics industry, solid-state lighting and for the curing of polymers and printing ink. The present invention therefore also relates to the use of the electroluminescent devices according to the invention in the said areas.

The devices according to the invention can also be employed for the light therapy (phototherapy) of humans and/or animals. The present invention therefore furthermore relates to the use of the devices according to the invention for the treatment, prophylaxis and diagnosis of diseases by means of phototherapy. The present invention still furthermore relates to the use, of the devices according to the invention for the treatment and prophylaxis of cosmetic conditions by means of phototherapy.

Phototherapy or light therapy is used in many areas of medicine and/or cosmetics. The devices according to the invention can therefore be employed for the therapy and/or prophylaxis and/or diagnosis of all diseases and/or in cosmetic applications for which the person skilled in the art considers using phototherapy. Besides irradiation, the term phototherapy also includes photo-dynamic therapy (PDT) as well as preservation, disinfection and sterilisation in general. It is not only humans or animals that can be treated by means of phototherapy or light therapy, but also any other type of living or non-living materials. These include, for example, fungi, bacteria, microbes, viruses, eukaryotes, prokaryotes, foods, drinks, water, drinking water, cutlery, medical instruments and equipment and other devices.

The term phototherapy also includes any type of combination of light therapy and other types of therapy, such as, for example, treatment with active compounds. Many light therapies have the aim of irradiating or treating exterior parts of an object, such as, for example, the skin of humans and animals, wounds, mucous membranes, the eye, hair, nails, the nail bed, gums and the tongue. In addition, the treatment or irradiation according to the invention can also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers, and desensitisation of the skin.

Particular preference is given for the purposes of the invention to the treatment and/or prophylaxis of psoriasis, acne, cellulite, skin wrinkling, skin ageing, jaundice and vitiligo.

Further areas of application according to the invention for the devices are selected from the group of inflammatory diseases, rheumatoid arthritis, pain therapy, treatment of wounds, neurological diseases and conditions, oedema, Paget's disease, primary and metastasising tumours, connective-tissue diseases or changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the devices are selected from winter depression, sleeping sickness, irradiation for improving the mood, the reduction in pain particularly muscular pain caused by, for example, tension or joint pain, elimination of the stiffness of joints and the whitening of the teeth (bleaching).

Further areas of application according to the invention for the devices are selected from the group of disinfections. The devices can be used for the treatment of any type of objects (non-living materials) or subjects (living materials such as, for example, humans and animals) for the purposes of disinfection, sterilisation or preservation. This includes, for example, the disinfection of wounds, the reduction in bacteria, the disinfection of surgical instruments or other articles, the disinfection or preservation of foods, of liquids, in particular water, drinking water and other drinks, the disinfection of mucous membranes and gums and teeth. Disinfection here is taken to mean the reduction in the living microbiological causative agents of undesired effects, such as bacteria and germs.

The devices according to the invention emit, in particular, in the UV and blue region of the spectrum. The precise wavelength can be adjusted towards longer wavelengths without difficulties by the person skilled in the art depending on the respective application.

In a particularly preferred embodiment of the present invention, the device is an organic light-emitting diode (OLED) or an organic light-emitting electrochemical cell (OLEC) which are employed for the purposes of phototherapy. Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, sleeves, blankets, hoods, sleeping bags, textiles and stents.

The use of the said devices for the said therapeutic and/or cosmetic purpose is particularly advantageous compared with the prior art, since homogeneous irradiation in the high-energy blue region and/or in the UV region of lower irradiation intensities is possible at virtually any site and at any time of day with the aid of the devices according to the invention using the OLEDs and/or OLECs. The irradiation can be carried out as an inpatient, as an outpatient and/or by the patient themselves, i.e. without introduction and/or guidance by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for re-use or be disposable articles, which can be disposed of after use once, twice or more times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

The present invention therefore also relates, in particular, to the device according to the invention for use in medicine for phototherapy.

The present invention also relates to the device according to the invention for use for the treatment of the skin by means of phototherapy.

The present invention also relates to the device according to the invention for use for the treatment of psoriasis by means of phototherapy.

The present invention also relates to the device according to the invention for use for the treatment of jaundice by means of phototherapy.

The present invention also relates to the device according to the invention for use for the treatment of jaundice of the newborn by means of phototherapy.

The present invention also relates to the device according to the invention for use for the treatment of acne by means of phototherapy.

The present invention also relates to the device according to the invention for use for the treatment of inflammation by means of phototherapy.

The present invention also relates to the device according to the invention for use for the treatment of atopic eczema by means of phototherapy.

The present invention also relates to the device according to the invention for use for the treatment of skin ageing by means of phototherapy The present invention furthermore relates to the use of the devices according to the invention in the cosmetics area for phototherapy.

In particular, the present invention relates to the use of the devices according to the invention for the phototherapeutic reduction and/or for the phototherapeutic prevention of the formation of skin wrinkles and skin ageing.

The present invention also relates to a method for the treatment of the skin by phototherapy using a device according to the invention.

For the purposes of the present invention, a straight-chain or branched or cyclic alkyl group or an aliphatic hydrocarbon radical is taken to mean an alkyl, alkenyl and alkynyl groups preferably having 1 or 3 to 40 C atoms respectively, more preferably 1 or 3 to 20 C atoms respectively. Cyclic alkyl groups can be mono-, bi- or polycyclic alkyl groups. Individual —CH— or —CH$_2$ groups may be replaced by N, NH, 0 or S. Examples of alkyl groups are the radicals methyl, ethyl, n-propyl, i-propyl, n-butyl, i-butyl, s-butyl, t-butyl, 2-methylbutyl, n-pentyl, s-pentyl, t-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl.

An alkoxy group or thioalkyl group is taken to mean an alkyl group as defined above which is bonded via an oxygen atom or a sulfur atom. Preferred alkoxy groups are methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. Preferred thioalkyl groups are methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethyl-thio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

In general, alkyl, alkoxy or thioalkyl groups or aliphatic hydrocarbon radicals in accordance with the present invention can be straight-chain, branched or cyclic, where one or more non-adjacent CH$_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, SO$_2$, NR$^1$, O, S or CONR$^1$; furthermore, one or more H atoms may also be replaced by D, F, Cl, Br, I, CN or NO$_2$, preferably F, Cl or CN, further preferably F or CN, particularly preferably CN.

The mono- or polycyclic aliphatic ring system can be a ring system which only consists of CH$_2$ units, but one or more of the CH$_2$ groups may also be replaced by O, S or NH.

An aromatic or heteroaromatic hydrocarbon radical can be mono- or polycyclic and preferably contains 6 or 5 to 20, more preferably 6 to 10, most preferably 5 or 6 aromatic ring atoms. If the unit is an aromatic unit, it preferably contains 6 to 20, more preferably 6 to 10, most preferably 6 carbon atoms as ring atoms. If the unit is a heteroaromatic unit, at least one of the ring atoms is a heteroatom. The heteroatoms are preferably selected from N, O and/or S. An aromatic or heteroaromatic unit here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, benzothiophene, benzofuran and indole etc.

Examples according to the invention of the aromatic or heteroaromatic unit are accordingly: benzene, naphthalene, anthracene, phenanthrene, pyrene, chrysene, benzanthracene, perylene, naphthacene, pentacene, benzopyrene, furan, benzofuran, isobenzofuran, dibenzofuran, thiophene, benzothiophene, isobenzothiophene, dibenzothiophene, pyrrole, indole, isoindole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system having 6 to 18 ring atoms, preferably 6 to 15 ring atoms and even more preferably 6 to 10 ring atoms is taken to mean a system which contains no aromatic heteroatoms. This system is not necessarily taken to mean only one which contains aromatic groups, but also one in which, in addition, a plurality of aromatic groups may be interrupted by a short non-aromatic unit (<10% of the atoms other than H, preferably <5% of the atoms other than H), such as, for example, sp$^3$-hybridised C, O, N, etc. These aromatic ring systems may be monocyclic or polycyclic, i.e. they may have one ring (for example phenyl) or two or more rings, which may also be condensed (for example naphthyl) or covalently linked (example biphenyl), or contain a combination of condensed and linked rings.

Preferred aromatic ring systems are, for example, phenyl, biphenyl, triphenyl, naphthyl, anthracyl, phenanthryl, dihydrophenanthryl, pyrene, dihydropyrene, chrysene, tetracene, fluorene and indole.

A heteroaromatic ring system in the sense of this invention is preferably taken to mean a heteroaromatic ring system having 5 to 18 ring atoms, preferably 5 to 14, particularly preferably 5 to 10 ring atoms. The heteroaromatic ring system contains at least one heteroatom selected from N, O and S (remaining atoms are carbon). A heteroaromatic ring system is, in addition, intended to be taken to mean a system which does not necessarily contain only aromatic or heteroaromatic groups, but also in which, in addition, a plurality of aromatic or heteroaromatic groups may be interrupted by a short non-aromatic unit (<10% of the atoms other than H, preferably <5% of the atoms other than H), such as, for example, sp$^3$-hybridised C, O, N, etc. These heteroaromatic ring systems may be monocyclic or polycyclic, i.e. they may have one ring (for example pyridyl) or two or more rings, which may also be condensed or covalently linked, or contain a combination of condensed and linked rings Preferred heteroaromatic ring systems are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene or combinations of these groups. Particular preference is given to imidazole, benzimidazole and pyridine.

The devices, compositions and formulations according to the invention are distinguished by the following surprising advantages over the prior art:

1. The devices according to the invention emit in the UV-A and UV-B region.
2. The emitter compounds required for the preferred emission are readily accessible.
3. The use of mixed hosts enables the operating voltage to be reduced and the radiation intensity to be increased.
4. The use of blocking layers enables the operating voltage to be significantly reduced and the radiation intensity to be increased.
5. The devices according to the invention can easily be processed from solution.

These above-mentioned advantages are not accompanied by an impairment in the other electronic properties.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples and FIGS. 1 to 4 without wishing to restrict it thereby.

EXAMPLES

Materials Used

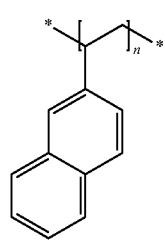

E1

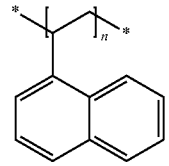

E2

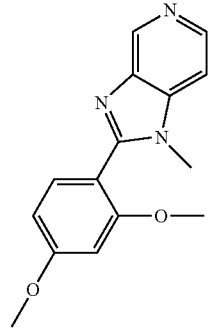

E3

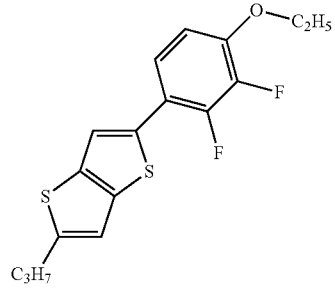

E4

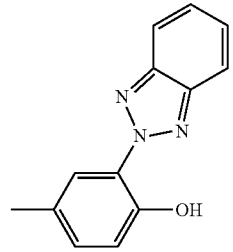

E5

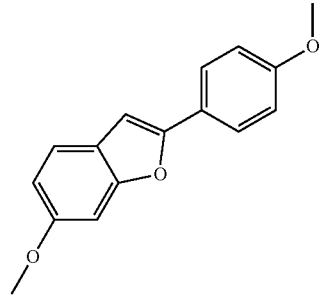

E6

E1 to E6 are compounds of the general formula (1) or (2).

E1 (poly(2-vinylnaphthalene)) and E2 (poly(1-vinylnaphthalene)) are obtainable from Sigma-Aldrich.

E3 (CAS: 87359-59-9) is commercially available (Ambinter).

E4 can be prepared by the process disclosed in Organic Letters, 2011 Vol. 13, No. 15 p 4100-4103.

E5 (CAS: 2440-22-4) is commercially available (abcr GmbH & Co. KG),

E6 (CAS: 1838-44-4) can be prepared in accordance with Organic Letters, 2009 Vol. 11, No. 23 p 5478-5481.

In addition, polystyrene (PS) from Fluka having a molecular weight Mw of 200 kdaltons is used.

H1 and H2, as follows, are employed as host compounds. The synthesis of H1 and H2 is carried out in accordance with DE 19927627.

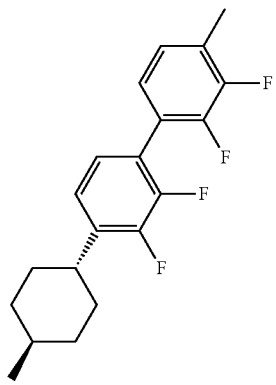

H1

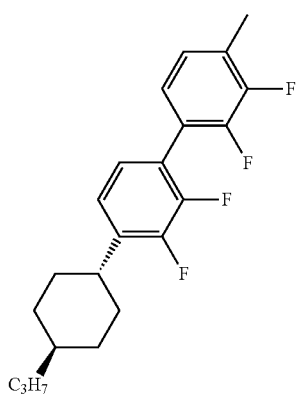

H2

Example 1: Quantum-Chemical Calculations

The HOMO (highest occupied molecular orbital) and LUMO (lowest unoccupied molecular orbital) energy as well as the triplet/singlet level and oscillator strength of the organic compounds are determined via quantum-chemical calculations. To this end, the "Gaussian03W" program package (Gaussian Inc.) is used. In order to calculate organic substances without metals, firstly a geometry optimisation is carried out by means of the semi-empirical "Ground State/Semi-empirical/Default Spin/AM1" method (Charge 0/Spin Singlet). An energy calculation is subsequently carried out on the basis of the optimised geometry. In this, the "TD-SCF/DFT/Default Spin/B3PW91" method with the "6-31G (d)" base set (Charge 0/Spin Singlet) is used. The most important results are HOMO/LUMO levels, energies for the triplet (T) and singlet (S) excited states and the oscillator strength (f). The first excited states ($S_1$ and $T_1$) are the most important here. $S_1$ stands for the first excited singlet level and $T_1$ stands for the first excited triplet level. The energy calculation gives the HOMO HEh or LUMO LEh in hartree units. The HOMO and LUMO values in electron volts (eV) are determined therefrom as follows, where these relationships arise from the calibration with reference to cyclic voltammetry measurements (CV):

HOMO(eV)=((HEh*27.212)−0.9899)/1.1206

LUMO(eV)=((LEh*27.212)−2.0041)/1.385

For the purposes of this application, these values are to be regarded as the energetic position of the HOMO level or LUMO level of the materials. As an example, an HOMO of −0.21401 hartrees and an LUMO of −0.03463 hartrees are obtained from the calculation for compound E1 (see also Table 1), which a calibrated HOMO of −6.06 eV, a calibrated LUMO of −2.19 eV.

It is known to the person skilled in the art that the quantum-chemical calculations, as described here, can be employed very well for the said purposes. The calculations give results which correlate very well with experimentally determined data.

TABLE 1

Energy levels of compounds E1 to E6

| Material | HOMO [eV] | LUMO [eV] | S1 [eV] | f |
|---|---|---|---|---|
| E1 | −6.06 | −2.19 | 4.31 | 0.08 |
| E2 | −6.08 | −2.13 | 4.24 | 0.03 |
| E3 | −6.12 | −2.08 | 4.25 | 0.37 |
| E4 | −5.73 | −2.35 | 3.93 | 0.91 |
| E5 | −6.37 | −2.51 | 3.79 | 0.14 |
| E6 | −5.33 | −2.15 | 3.81 | 1.09 |

Example 2: Solutions and Compositions

Solutions, as summarised in Table 2, are prepared as follows: firstly, the mixtures of host and emitter are dissolved in 10 ml of toluene with a concentration of 16 mg/ml and stirred until the solution is clear. The solution is filtered using a Millipore Millex LS, hydrophobic PTFE 5.0 μm filter.

TABLE 2

Compositions of the solutions

| | Composition | Ratio (based on weight) | OLED |
|---|---|---|---|
| Solution Ref1 | E1 | 100% | OLED Ref1 |
| Solution Ref2 | E2 | 100% | OLED Ref2 |
| Solution 1 | H1:H2:PS:E1 | 30%:30%:20%:20% | OLED1 |
| Solution 2 | H1:H2:PS:E2 | 30%:30%:20%:20% | OLED2 |
| Solution 3 | H1:H2:PS:E3 | 30%:30%:30%:10% | OLED3 |

PS stands for polystyrene;

The solutions are used in order to coat the emitting layer of OLEDs. The corresponding solid composition can be obtained by evaporating the solvent from the solutions. This can be used for the preparation of further formulations.

Example 3: Production of the OLEDs

OLED-Ref1 OLED-Ref2, OLED1-3 have the following structure: ITO/PEDOT/EML/cathode, where EML stands for the emission layer and ITO stands for the anode (indium tin oxide).

The OLEDs are produced using the corresponding solutions, as summarised in Table 2, in accordance with the following procedure:

1) Coating of 80 nm of PEDOT (CLEVIOS™ HIL 1.3) onto an ITO-coated glass substrate by spin coating; drying by heating at 180° C. for 10 min. in a clean room.

2) Coating of an 80 nm emitting layer by spin coating of one of the solution in accordance with Table 2 in a glove box.
3) Drying of the device by heating: 10 min at 180° C. for OLED Ref1 and OLED Ref2 in a glove box; for OLED1-3 30 min at 50° C. and then 30 min in vacuo.
4) Vapour deposition of a Ba/Al cathode (3 nm/150 nm).
5) Encapsulation of the device.

Example 4: Characterisation of the OLEDs

Firstly, photoluminescence spectra of the emission layer (EML) and subsequently electroluminescence spectra (EL) of the OLEDs obtained in this way are measured, since the EL spectrum gives the most important indications of a functioning electroluminescent device.

The EL spectra are measured by means of Ocean Optics UBS2000.

Figure 2:
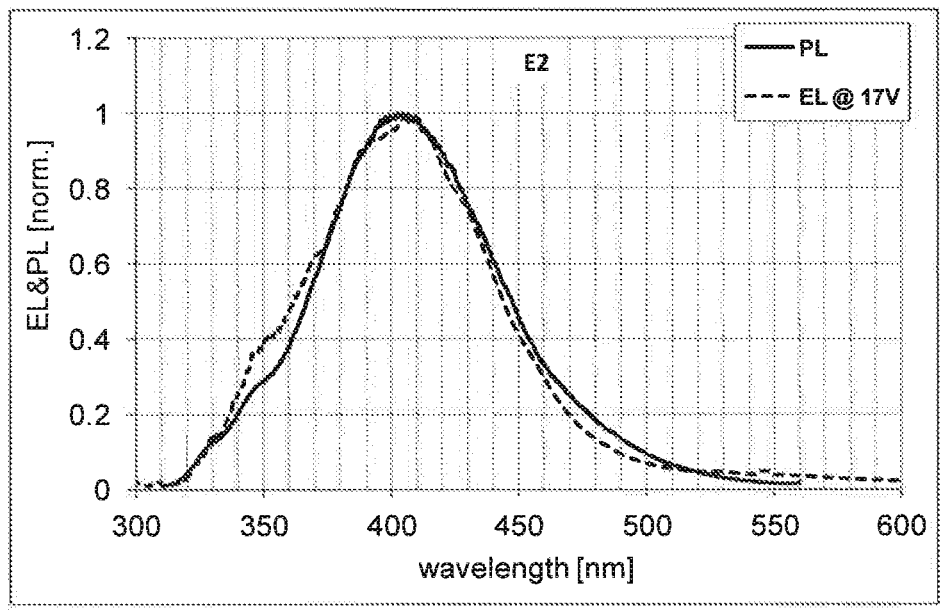
Figure 3:
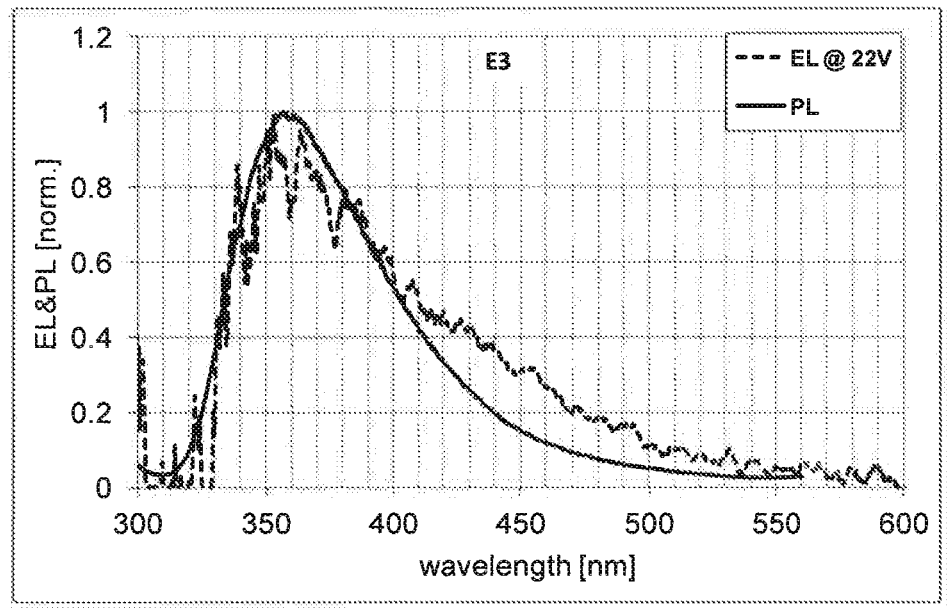

The EL spectra of OLED1-3 are summarised in FIG. 1-3. For OLED Ref1 and OLED Ref2, no EL spectra can be measured, even if the voltage is increased to 40 V. However, the OLEDs comprising emitters E1 to E3 according to the invention, or the mixtures according to the invention, like exhibit a clear EL spectrum having a significant proportion between 280 to 380 nm.

The PL spectra in FIGS. 1-3 were measured in an 80 nm layer which have been applied to quartz using corresponding solutions in Table 2 by spin coating It is in fact very surprising that the emitters according to the invention have emitted in the UV region in an OLED having the simple layer structure indicated and comprising polystyrene as host. It is apparent that the person skilled in the art will be able to carry out further optimisations on the basis of the present invention and without inventive step.

Figure 4:
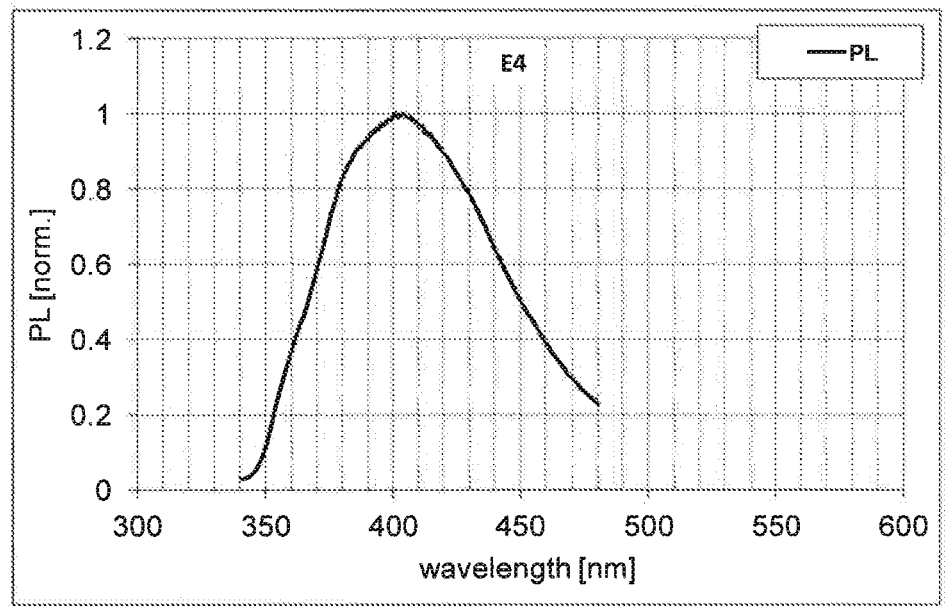
FIG. 4 shows the photoluminescence spectrum of emitter E4.

For E4, only PL spectrum was measured, which FIG. 4 shows. The PL spectra of V4 were measured in an 80 nm thick layer of PS:E4 (30% by weight, based on the entire layer) on quartz. The has all significant parts in the UV region.

Further improvements according to the invention can be achieved through the use of a "mixed host", an additional blocking layer or buffer layer.

Example 5: Synthesis of the Side-Chain Polymers P1 to P10

Synthesis of P1:
0.314 g (2.175 mmol) of 6-ethenylbenzofuran (CAS 1158745-25-5) and 0.228 g (2.175 mmol) of styrene (CAS 100-42-5) are transferred into a dried flask and rendered inert. 2.3 ml of degassed, dry toluene are added, and the solution is rendered inert a number of times. In a separate Schlenk vessel, 0.7 mg (0.004 mmol) of α,α'-azoisobutyronitrile are dissolved in 10 ml of dry, degassed toluene and rendered inert. The monomer solution is warmed to 70° C., and 0.1 ml of the AIBN solution is added to the reaction solution by means of a syringe. The reaction mixture is stirred at 70° C. for 72 h, then cooled to room temperature and stirred for a further 24 h. The reaction mixture is added dropwise to degassed ethanol, and the solid formed is filtered off. The solid is re-dissolved in toluene and precipitated in ethanol. The solid is filtered off and dried at 40° C. in a high vacuum for 24 h.

Polymers P2 to P10 (Examples 2 to 10) can be obtained analogously to P1:

| Ex. | Starting material | Starting material | Product | Yield |
|---|---|---|---|---|
| 1 | CAS 1158745-25-5 | CAS 100-42-5 | P1 | 66% |
| 2 | CAS 1388025-45-3 | CAS 100-42-5 | P2 | 57% |

-continued
| Ex. | Starting material | Starting material | Product | Yield |
|---|---|---|---|---|
| 3 | 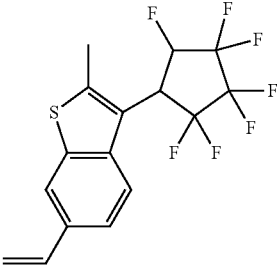<br>CAS 167890-09-7 | 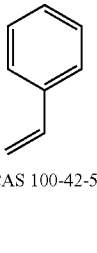<br>CAS 100-42-5 | P3<br>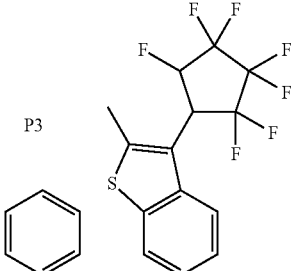 | 45% |
| 4 | <br>CAS 1057661-21-8 | 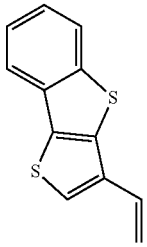<br>CAS 100-42-5 | P4<br>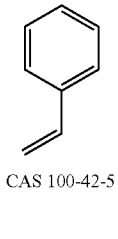 | 63% |
| 5 | 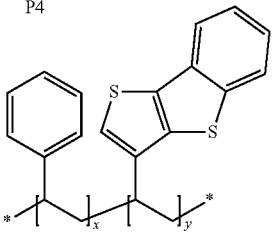<br>CAS 59208-04-7 | 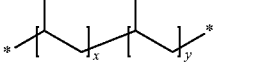<br>CAS 100-42-5 | P5<br>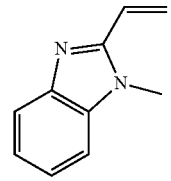 | 70% |
| 6 | 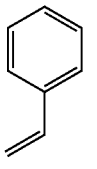<br>CAS 68526-80-2 | 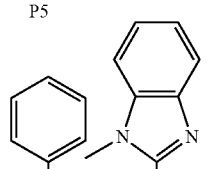<br>CAS 100-42-5 | P6<br>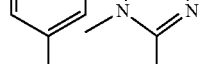 | 75% |
| 7 | 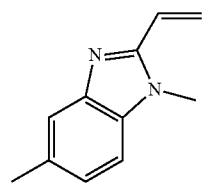<br>CAS 68526-81-3 | 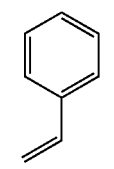<br>CAS 100-42-5 | P7<br>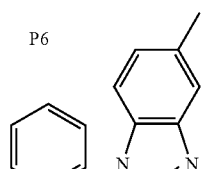 | 73% |

-continued

| Ex. | Starting material | Starting material | Product | Yield |
|---|---|---|---|---|
| 8 | <br>CAS 151920-64-8 | 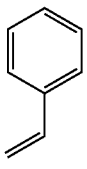<br>CAS 100-42-5 | P8<br>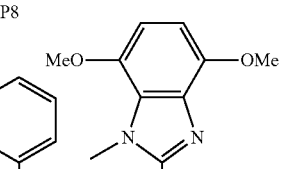 | 84% |
| 9 | 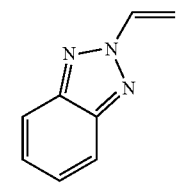<br>CAS 116477-12-4 | 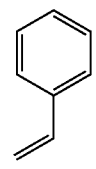<br>CAS 100-42-5 | P9<br>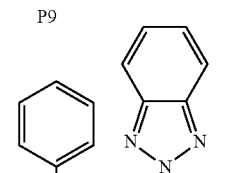 | 42% |
| 10 | 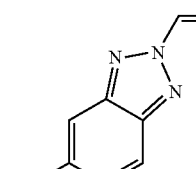<br>CAS 116477-12-4 | 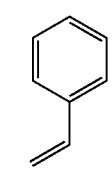<br>CAS 100-42-5 | P10<br>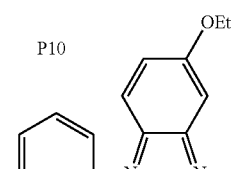 | 69% | x = 0.5, y = 0.5

The PL spectra of P1-10 in toluene solutions having a concentration of 5 mg/ml are measured. All polymers exhibit a clearly emission in wavelength range from 310 to 380 nm.

The invention claimed is:
1. An organic electroluminescent device comprising at least two electrodes and at least one emitting layer between the electrodes which comprises at least one bi- or tricyclic aromatic or heteroaromatic compound of the general formulae (130) to (137):

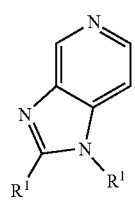

formula (130)

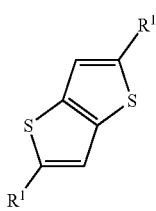

formula (131)

-continued

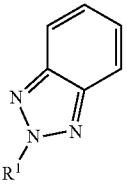

formula (132)

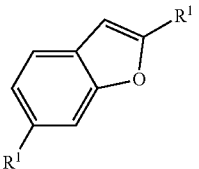

formula (133)

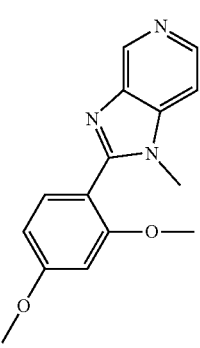
formula (134)

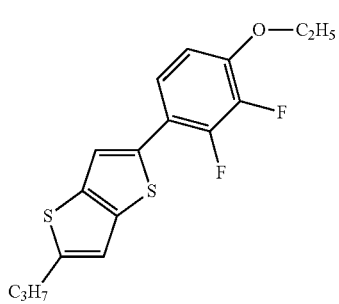
formula (135)

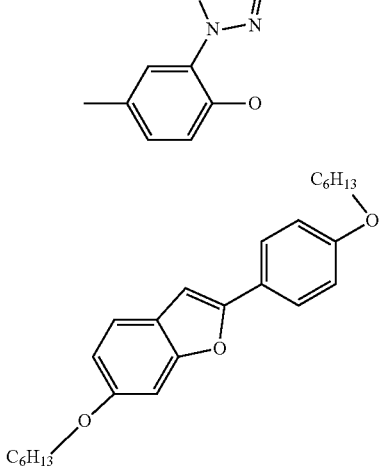
formula (136)

formula (137)

where one or more H atoms of these compounds is replaced by one, two, three or four of a radical $R^1$, $R^1$ is, identically or differently on each occurrence, D, F, $N(R^2)_2$, $Si(R^2)_3$, $B(OR^2)_2$, $P(R^2)_2$, $S(=O)R^2$, a straight-chain alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C=CR^2$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by D, F, Cl, or CN, or an uncondensed aromatic ring system having 6 to 18 aromatic ring atoms or an uncondensed heteroaromatic ring system having 5 to 18 aromatic ring atoms, each of which is optionally substituted by one or more radicals $R^2$, or a condensed aromatic or heteroaromatic ring system having 8 to 12 aromatic ring atoms, which may in each case be substituted by one or more radicals $R^2$, or a combination of two or more of these groups, two or more substituents $R^1$ may also form a mono- or polycyclic aliphatic ring system with one another here;

$R^2$ is, identically or differently on each occurrence, H, D, F, OH, $N(R^3)_2$, $Si(R^3)_3$, $B(OR^3)_2$, $P(=O)(R^3)_2$, $P(R^2)_2$, $S(=O)R^3$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^3$, where one or more non-adjacent $CH_2$ groups is optionally replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl or CN, or an uncondensed aromatic ring system having 6 to 18 aromatic ring atoms or an uncondensed haeroaromatic ring system having 5 to 18 aromatic ring atoms, each of which be substituted by one or more radicals $R^3$, or a condensed aromatic or heteroaromatic ring system having 8 to 12 aromatic ring atoms, which may in each case be substituted by one or more radicals $R^3$, or a combination of two or more of these groups; two or more adjacent radicals $R^2$ may form a mono- or polycyclic aliphatic ring system with one another here; and $R^3$ is, identically or differently on each occurrence, H, D, F, a straight-chain alkyl, alkoxy or thioalkoxy group having 1 to 40 C atoms or a branched or cyclic alkyl, alkoxy or thioalkoxy group having 3 to 40 C atoms, an uncondensed aromatic ring system having 6 to 18 aromatic ring atoms or a heteroaromatic ring system having 5 to 12 aromatic ring atoms, in which, in addition, one or more H atoms is optionally replaced by F; two or more substituents $R^3$ may also form a mono- or polycyclic aliphatic ring system with one another here wherein the compound of the formulae (130) to (137) is employed as UV light-emitting compound, and wherein the device emits radiation having a wavelength in the range from 280 nm to 380 nm.

2. The electroluminescent device according to claim 1, wherein the device comprises one or more additional layers between the electrodes.

3. The electroluminescent device according to claim 2, wherein the additional layer is selected from the group consisting of the following:
   (a) an exciton-blocking layer which comprises an exciton-blocking material having a band gap of 3.6 eV or higher;
   (b) an electron-blocking layer which comprises an electron-blocking material having an LUMO of higher than −2.2 eV; and
   (c) a hole-blocking layer which comprises a hole-blocking material having an HOMO of lower than −6.0 eV.

4. The electroluminescent device according to claim 1, wherein the device is an organic light-emitting diode (OLED), a polymeric light-emitting diode (PLED), an organic light-emitting electrochemical cell (OLEC, LEEC or LEC), an organic light-emitting transistor (O-LET) or an organic light-emitting electrochemical transistor.

5. The electroluminescent device according to claim 4, wherein the device is an OLED, PLED or OLEC.

6. A device according to claim 1 for use in medicine for phototherapy.

7. A method for the treatment of the skin by phototherapy comprising utilizing the device according to claim 1.

8. The electroluminescent device according to claim 1, wherein
- $R^1$ being a straight-chain alkoxy group having 1 to 12 C atoms or an aromatic ring system having 6 to 10 aromatic ring atoms, each of which may be substituted by one or more radicals $R^2$, and
- $R^2$ is, identically or differently on each occurrence, D, F, $N(R^3)_2$, $Si(R^3)_3$, $B(OR^3)_2$, $P(=O)(R^3)_2$, $P(R^2)_2$, $S(=O)R^3$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^3$, where one or more non-adjacent $CH_2$ groups is optionally replaced by $R^3C=CR^3$, $Si(R^3)_2$, $Ge(R^3)_2$, $Sn(R^3)_2$, C=O, C=S, C=Se, C=$NR^3$, $P(=O)(R^3)$, SO, $SO_2$, $NR^3$, O, S or $CONR^3$ and where one or more H atoms is optionally replaced by D, F, Cl or CN, or an uncondensed aromatic ring system having 6 to 18 aromatic ring atoms or an uncondensed heteroaromatic ring system having 5 to 18 aromatic ring atoms, each of which be substituted by one or more radicals $R^3$, or a condensed aromatic or heteroaromatic ring system having 8 to 12 aromatic ring atoms, which may in each case be substituted by one or more radicals $R^3$, or a combination of two or more of these groups; two or more adjacent radicals $R^2$ may form a mono- or polycyclic aliphatic ring system with one another here.

9. The electroluminescent device according to claim 1, wherein $R^2$ being F, OH, or a straight-chain alkyl or alkoxy group having 1 to 12 C atoms.

10. The electroluminescent device according to claim 1, wherein $R^1$ is, identically or differently on each occurrence, D, F, $N(R^2)_2$, $Si(R^2)_3$, $B(OR^2)_2$, $P(R^2)_2$, $S(=O)R^2$, a straight-chain alkoxy or thioalkoxy group having 1 to 40 C atoms or a branched or cyclic alkoxy or thioalkoxy group having 3 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, C=$NR^2$, $P(=O)(R^2)$, SO, $SO_2$, $NR^2$, O, S or $CONR^2$ and where one or more H atoms is optionally replaced by D, F, Cl, or CN, or an uncondensed aromatic ring system having 6 to 18 aromatic ring atoms or an uncondensed heteroaromatic ring system having 5 to 18 aromatic ring atoms, each of which is optionally substituted by one or more radicals $R^2$, or a condensed aromatic or heteroaromatic ring system having 8 to 12 aromatic ring atoms, which may in each case be substituted by one or more radicals $R^2$.

* * * * *